US006852269B2

(12) United States Patent
Eberle et al.

(10) Patent No.: US 6,852,269 B2
(45) Date of Patent: Feb. 8, 2005

(54) PROCESS FOR APPLYING A CUSHION MATERIAL TO AN ARTICLE

(75) Inventors: John D. Eberle, Amherst, NY (US); Ryan Carlson, Buffalo, NY (US); Robert E. Orzukak, Niagra Falls, NY (US)

(73) Assignee: Silipos, Inc., New York, NY (US)

( * ) Notice: Subject to any disclaimer, the term of this patent is extended or adjusted under 35 U.S.C. 154(b) by 0 days.

(21) Appl. No.: 10/102,377

(22) Filed: Mar. 19, 2002

(65) Prior Publication Data

US 2003/0178746 A1 Sep. 25, 2003

(51) Int. Cl.[7] ............................................. B29C 41/12
(52) U.S. Cl. .................... 264/512; 264/102; 264/257; 264/258; 264/266; 264/267; 264/325; 156/245
(58) Field of Search .................. 264/510, 511, 264/512, 101, 102, 257, 258, 266, 267, 299, 319, 313, 324, 325, 219; 156/245

(56) References Cited

U.S. PATENT DOCUMENTS

| | | | |
|---|---|---|---|
| 3,165,569 A | * 1/1965 | Bright | 264/313 |
| 4,114,200 A | 9/1978 | Smith et al. | 2/51 |
| 4,456,642 A | * 6/1984 | Burgdorfer et al. | 428/68 |
| 5,507,834 A | * 4/1996 | Laghi | 623/36 |
| 5,590,820 A | * 1/1997 | Plastino | 223/12 |
| 5,603,122 A | 2/1997 | Kania | 2/239 |
| 5,672,305 A | * 9/1997 | Kogure | 264/102 |
| 5,830,237 A | * 11/1998 | Kania | 623/37 |
| 5,910,059 A | 6/1999 | Hanson | 473/594 |
| 6,017,407 A | * 1/2000 | Yates | 156/221 |
| 6,117,259 A | * 9/2000 | Yates | 156/145 |

FOREIGN PATENT DOCUMENTS

| | | |
|---|---|---|
| EP | 0234796 | 9/1987 |
| WO | WO9804218 | 2/1998 |

* cited by examiner

Primary Examiner—Stefan Staicovici
(74) Attorney, Agent, or Firm—Darby & Darby

(57) ABSTRACT

A process for forming a cushion layer of a preselected thickness on an inside of a prosthetic liner body is provided and includes the steps of introducing the liner body into a mold cavity; disposing a sufficient amount of cushioning material into the inside of the liner and directing a mandrel into the inside of the liner body. The driving action of the mandrel causes the cushioning material to be dispersed between the mandrel and the liner body, thereby forming the cushioning layer of preselected thickness.

40 Claims, 13 Drawing Sheets

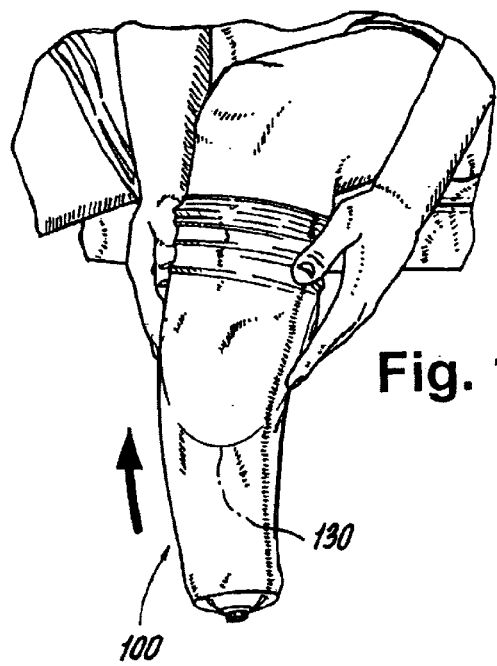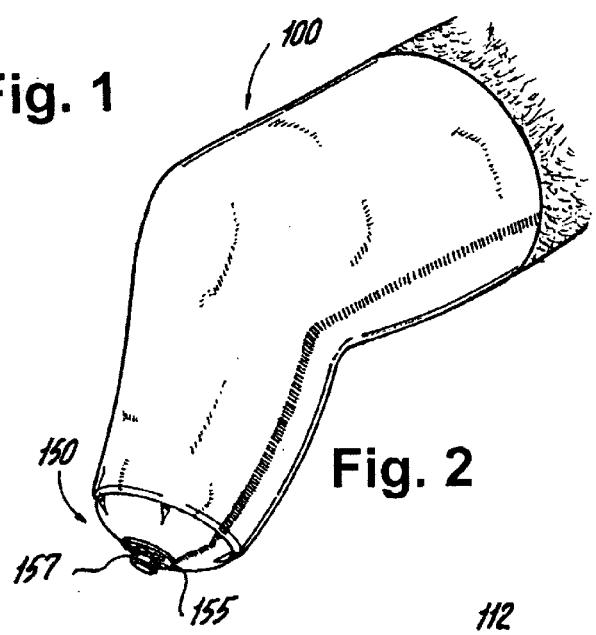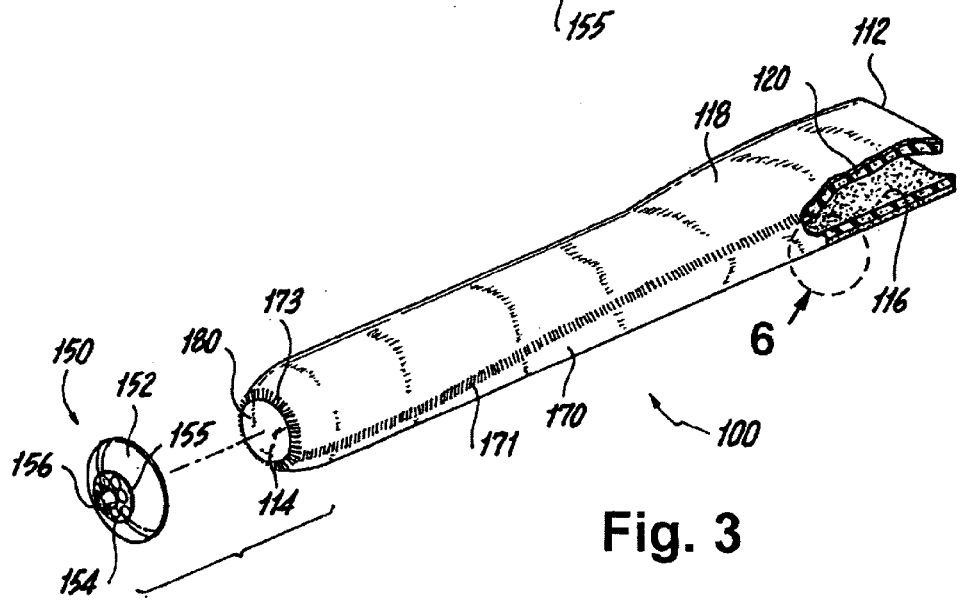

Fig. 4
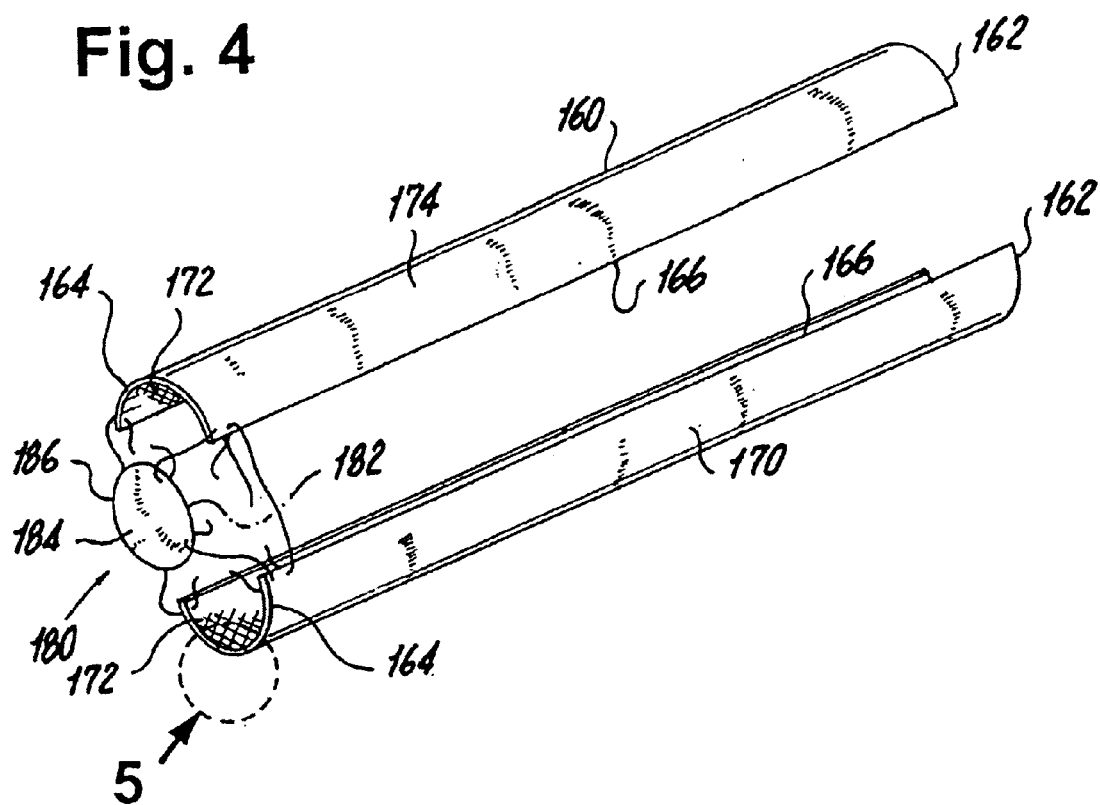
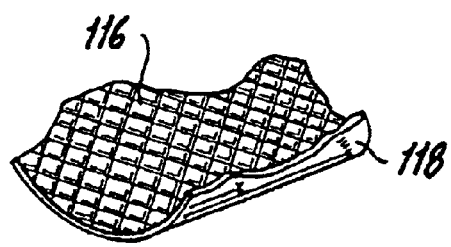
Fig. 5
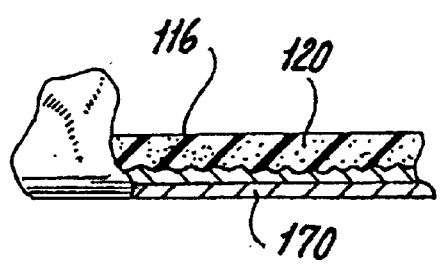
Fig. 6

Fig. 16
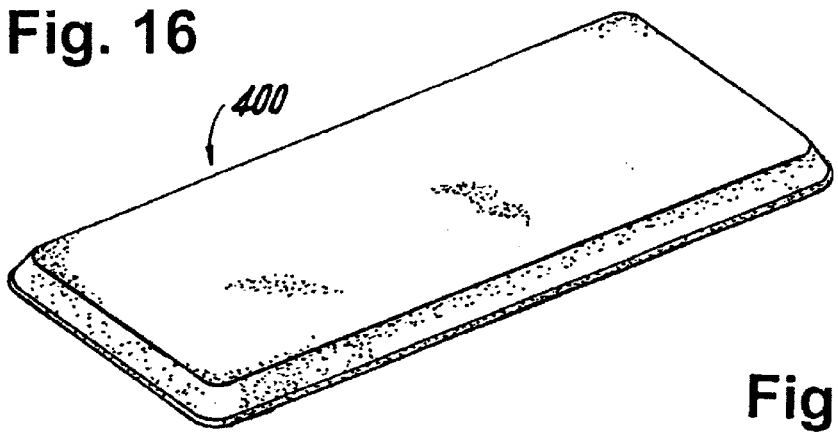
Fig. 17
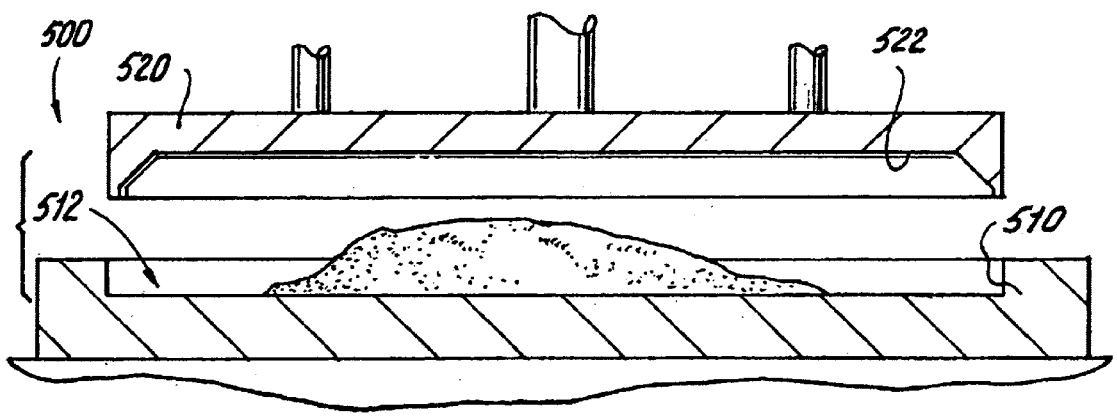
Fig. 18
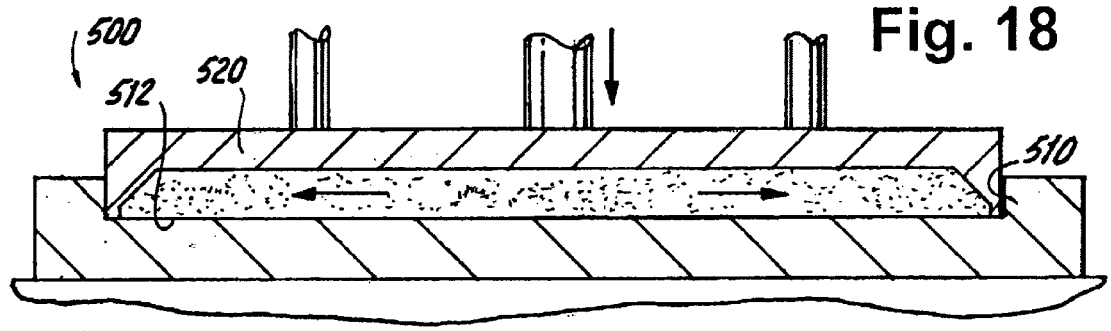
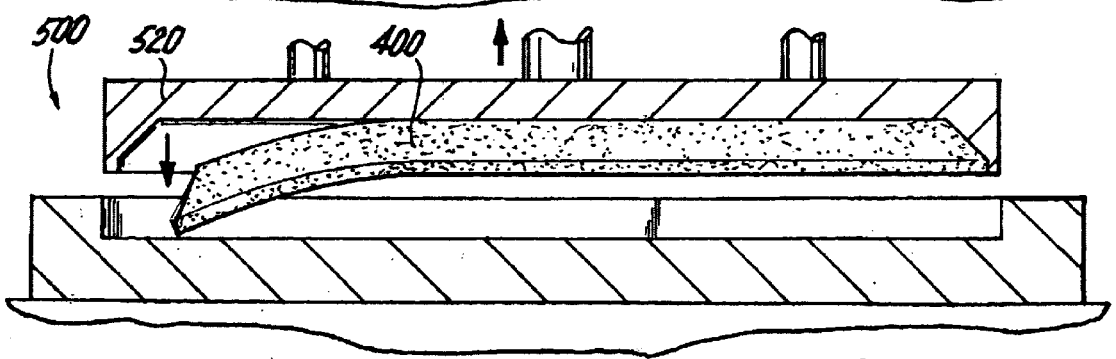
Fig. 19

PROCESS FOR APPLYING A CUSHION MATERIAL TO AN ARTICLE

TECHNICAL FIELD

The present invention relates generally to a process for forming a cushioned article having a predetermined thickness and contour and more particularly, to a process for applying a gel-like cushioning material to an inside of a liner body to form a cushioned liner that is constructed to be worn over an amputee's residual limb.

BACKGROUND

For the past decades, amputees have worn tubular sock-like articles over their residual limbs to provide additional comfort to the amputee when wearing a prosthetic limb. For many years, the tubular sock-like articles were formed of natural materials, such as cotton, wool, and cotton-wool blends; however, as synthetic materials become increasingly popular as a material of choice to form articles of apparel, including socks, the tubular sock-like articles were increasingly fabricated using synthetic materials.

As is known, an amputee is typically fitted with a prosthetic member to be worn on the residual limb. In a below-knee (BK) prosthesis, an amputee's stump tends to pivot within a socket of the prosthesis. During ambulation, the stump will come up in the socket of the prosthesis until the means for attaching the prosthetic to the wearer causes the prosthetic to lift with the stump. The wearer then completes a walking motion or other movement by repeatedly lifting the prosthetic up and then placing it back down in a different location to effectuate movement of the wearer's body.

Most of the available cushioned residuum socks (prosthetic liners) that are currently available have a tubular or conical construction and do not provide a form fit of the amputee's residuum since the residuum stump typically does not contain a completely uniform shape. For example, while the residuum stump generally has a roughly conical shape, the residuum stump will often have recessed areas in certain locations. On a below knee, left side residual limb, the recessed area is often more pronounced on the right side of the tibia bone, while for right side residual limbs, the more pronounced recessed area is on the left side of the bone. In both instances, the side opposite the side with the more pronounced recessed area will also contain a recessed area to a lesser degree and further the greatest recess typically occurs immediately below the patella, one either side. Conventional prosthetic liners do not accommodate the non-uniform nature of the residuum and this can result in the amputee experiencing wearing discomfort due to the non-uniform fit.

When the amputee uses a prosthetic device, the amputee simply attaches a prosthetic limb to their residual limb by means of a rigid socket, liner, and a suspension means. The rigid socket can be custom fabricated to match the shape of the intended user's residual limb and can be formed from a variety of different materials, including but not limited to thermoplastic materials, fiber-reinforced thermoset materials, as well as wood and metals. Because the residual limb interfaces with the hard, rigid prosthetic limb, this interface can become an area of discomfort over time since this interface is a load bearing interface between the residual limb and the prosthetic limb. In order to alleviate this discomfort and provide a degree of cushioning to lessen the impact of the load, prosthetic liners (socks) are used as interface members between the hard prosthetic socket and the residual limb in order to increase comfort.

Traditionally, several methods have been used to apply a cushion material to an article, such as a sleeve member intended for use as a prosthetic liner for placement over a residual limb. One process uses conventional dipping techniques in which the closed distal end of the sleeve member is dipped into cushioning material which exists in a liquid or molten state. The sleeve member is dipped into the cushioning material at a prescribed angle relative to the surface of the molten or liquified cushioning material so that the cushioning material extends up the sleeve member from the closed distal end to a further extent on the side of the sleeve member. The sleeve member is then manipulated in the liquified or molten cushioning material to effectively coat the surface of the sleeve member with the cushioning material. When the cushioning material is applied in this manner, the sleeve member has likely been inverted so that the interior surface is actually the exterior surface that is exposed to the liquified or molten cushioning material. After application of the cushioning material by dipping the inverted sleeve member into the liquified or molten cushioning material and permitting the cushioning material to sufficiently cool, the coated sleeve member is then inverted again so that the surface that has the cushioning material applied thereon becomes the interior surface of the cushioned sleeve member.

Prior to inserting (i.e., dipping) the sleeve member into the liquified or molten cushioning material, a mandrel or the like is inserted into the inverted sleeve member to stretch and shape the sleeve member to its intended tubular shape. The mandrel is thus a tool that permits a person to dip the sleeve member into the liquified or molten cushioning material without exposing the person to any unnecessary risks. The mandrel is then manipulated so that the exposed surfaces of the sleeve member are in contact with the cushioning material. In order to increase the thickness, the sleeve member is repeatedly dipped so as to effectively build-up the thickness of the cushioning material.

One of the disadvantages of the dipping process is that control of the thickness of the cushioning material is rather an arduous task and is fairly imprecise due to the thickness being built-up to a desired thickness by repeatedly dipping the sleeve member into the coating. Further, the sleeve member must be inverted before and after the cushioning material is applied to the sleeve member. After the cushioning material has been applied and allowed to cool, the final inversion of the cushioned sleeve member can cause crazing, folding or other imperfections to form in the layer of the cushioning material.

In addition to the application of the cushioning material to the sleeve member by dipping the sleeve member into liquified or molten cushioning material, the cushioning material can be "painted" onto the sleeve member or it is also possible to dissolve the polymeric material in a solvent followed by application of the solvent to the sleeve member with subsequent evaporation of the solvent, thereby leaving a layer of cushioning material formed on the sleeve member. This process is also marked by a degree of imprecision with respect to forming the cushioning material to a desired thickness.

Another process for applying a cushioning materials is an "open pour" process in which the cushioning material is poured into a mold and settles therein due to gravitational forces. This process does not involve compression of the material and is marked by the following disadvantages: it is difficult to precisely control the thickness and a poor bond typically results between the fabric and the material.

Further, all of the above-methods do not permit the thickness of the cushion layer to be specially contoured in select regions of the article for purpose of providing more or less comfort and protection in these regions.

Thus, there is still a need in the art for a simple yet effective process for applying a layer of cushioning material to a surface of an article, whereby the thickness of the cushion layer can be controlled to a high degree of precision and the profile of the cushion layer can also be controlled and varied depending upon the application.

SUMMARY

A number of different methods for applying a layer of cushioning material to a surface of an article are provided, whereby the thickness of the cushion layer can be controlled to a high degree of precision and the profile of the cushion layer can also be controlled and varied depending upon the application. In one exemplary embodiment, a process for forming a cushion layer of a preselected thickness on an inside of prosthetic liner body is provided. The process includes the steps of: (a) providing an apparatus including a mold having a cavity formed therein and a mandrel that is positionable between a retracted position and an extended position, wherein in the extended position, at least a portion of the mandrel is received within the cavity; (b) disposing the prosthetic liner body into the mold cavity; (c) disposing a quantity of cushioning material into the inside of the prosthetic liner such that the cushioning material pools at a distal end of the prosthetic liner, the quantity being a sufficient quantity to form the cushion layer of the preselected thickness; (d) directing the mandrel into the inside of the prosthetic liner until the mandrel is positioned in the extended position, the driving action of the mandrel causing the cushioning material to be dispersed between the mandrel and the prosthetic liner, thereby forming the cushioning layer of the preselected thickness; (e) cooling the cushioning material to form a cushioned prosthetic liner; and (f) withdrawing the mandrel from the mold cavity such that the cushioned prosthetic liner can be removed therefrom.

The present process is not limited to producing cushioned prosthetic liner; but rather can be used produce a number of different products, including but not limited cushioning pads with or without a fabric backing layer; cushioned elbow pads, cushioned socks, etc.

Because the distance between the mandrel and the prosthetic liner (or cavity wall in other embodiments) corresponds to the thickness of the cushioned article to be formed, the present process permits the thickness of the cushion layer to be controlled with enhanced precision since this distance between the mandrel and the prosthetic liner (or cavity wall) along its length is readily determinable and know and therefore, the precise thickness is readily controllable. The above process also permits the profile (contour) of the cushion layer to be readily changed by altering a surface of one of the mandrel and the cavity.

Other features and advantages of the present invention will be apparent from the following detailed description when read in conjunction with the accompanying drawings.

BRIEF DESCRIPTION OF THE DRAWINGS

The foregoing and other features of the present invention will be more readily apparent from the following detailed description and drawings of illustrative embodiments of the invention in which:

FIG. 1 is a perspective view of a cushioned prosthetic liner according to one exemplary embodiment being placed on a residual limb of an amputee;

FIG. 2 is a perspective view of the prosthetic liner of FIG. 1 with the residual limb being fully inserted into the prosthetic liner;

FIG. 3 is a partially exploded perspective view of the prosthetic liner of FIG. 1 with a section of the prosthetic liner being shown in cross-section;

FIG. 4 is an exploded perspective view of a sleeve member of the prosthetic liner illustrating exemplary points of attachment between the individual components;

FIG. 5 is a perspective an exemplary fabric taken from circle 5 of FIG. 4 used to form the individual components of the sleeve member of FIG. 4;

FIG. 6 is a cross-sectional view taken from circle 6 of FIG. 3;

FIG. 16 is a perspective view of a cushioned article;

FIG. 17 is a cross-sectional side elevational view of an exemplary apparatus for forming the article of FIG. 16 with a mandrel being shown in the retracted position;

FIG. 18 is cross-sectional side elevational view of the apparatus of FIG. 17 with the mandrel being in the fully extended position;

FIG. 19 is a cross-sectional side elevational view of the apparatus of FIG. 17 with the mandrel being retracted to permit removal of the article;

DETAILED DESCRIPTION OF THE PREFERRED EMBODIMENTS

Figure 7:
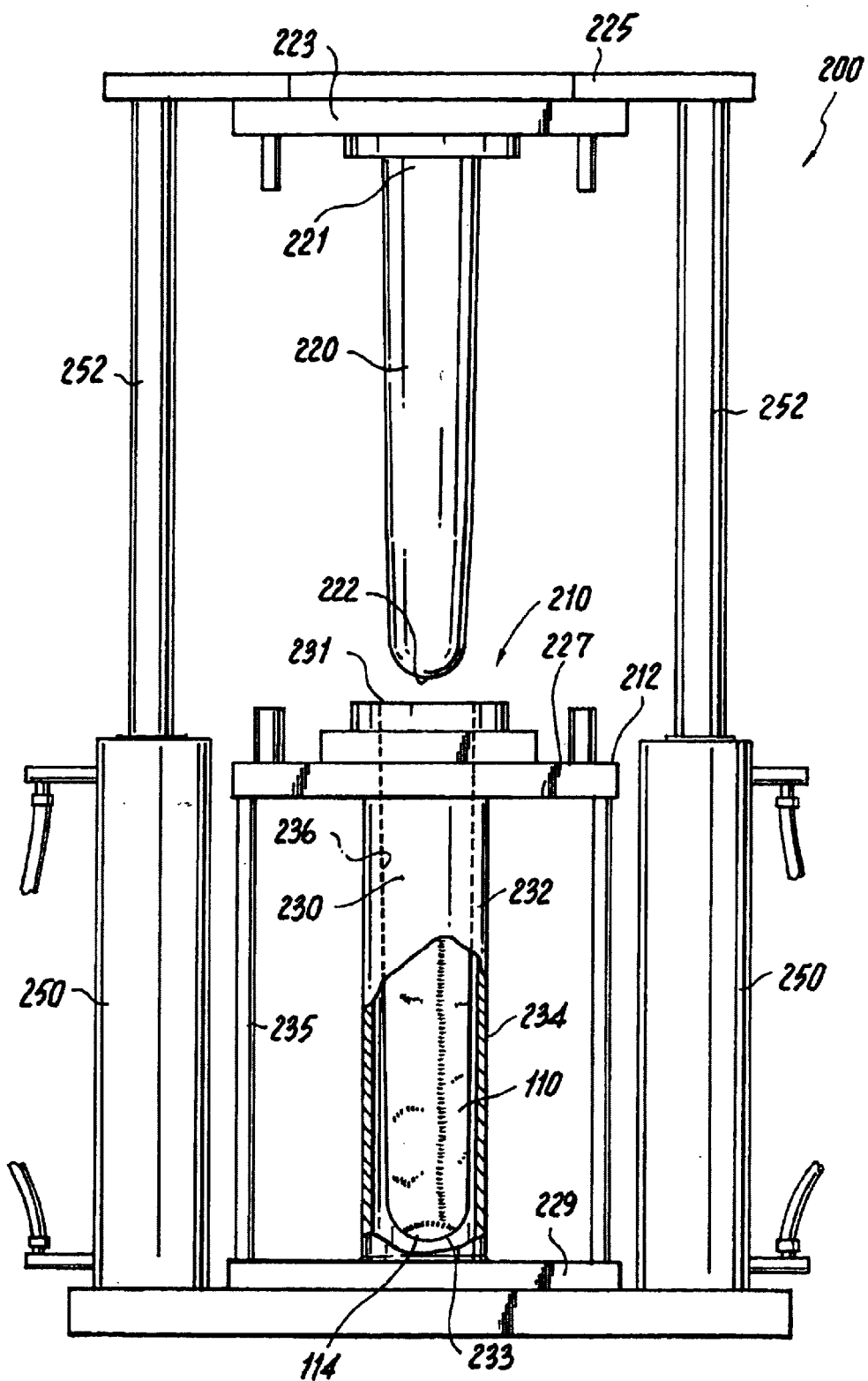
FIG. 7 is a side elevational view, in partial cross-section, of an apparatus for applying a cushioning material to a liner body to form the cushioned liner of FIG. 1.

Referring to FIGS. 1 through 6, a cushioned liner (e.g., a prosthetic liner) 100 according to one exemplary embodiment is illustrated. The cushioned liner 100 is formed of a liner body 110 having a form fitting generally tubular shape with an open end 112 into which an amputation stump (residual limb) 130 can be introduced and a closed distal end 114. The liner body 110 includes an interior 116 and an exterior 118 with the interior 116 being impregnated with a cushioning material to form a cushion layer 120 so as to provide a cushion between the amputee's residual limb 130 and a prosthetic device (not shown) which is to be attached to or otherwise coupled to the residual limb 130, as will be described in greater detail below.

When the cushioned liner 100 is used to couple a prosthetic device to the residual limb 130, a pin receptacle 150 is preferably provided and is attached to the distal end 114 of the cushioned liner 100 on the exterior 118 thereof. In the exemplary embodiment, the pin receptacle 150 has a resilient radial skirt portion 152 surrounding a receptacle body 154. The receptacle body 154 is a rigid member that is preferably formed of metal and includes a threaded bore 156 which threadingly receives a connecting member (e.g., a threaded pin) of the prosthetic device to securely attach the prosthetic device to the cushioned liner 100. The radial skirt portion 152 preferably has a diameter that is approximately equal to or less than the diameter of the distal closed end 114 of the liner body 110 so that the radial skirt portion 152 does not extend beyond the peripheral edge of the liner body 110 at the distal end 114 thereof. In other words, there should be a smooth radial interface between the radial skirt portion 152 and the liner body 110. However, in some applications, it may be desirable for the radial skirt portion 152 to extend beyond the peripheral edge of the liner body 110.

The radial skirt portion 152 is a flexible member that is formed of a resilient material, such as a polymeric material. The receptacle body 154 can be formed of any number of materials, such as metals, and in one embodiment, the receptacle body 154 is formed of aluminum.

The pin receptacle 150 is disposed at the closed distal end 114 of the liner body 110 using any number of techniques. When the pin receptacle 150 is disposed on the distal end 114, the receptacle body 154 is generally centered about the distal end 114. The receptacle body 154 has an annular base 155 (i.e., radial flange) that surrounds an annular boss 157 that includes the threaded bore 156. Preferably, the radial skirt portion 152 is formed over the receptacle body 154 and the polymeric material forming the radial skirt portion 152 surrounds the outer surface of the annular boss 157. In other words, the only portion of the receptacle body 154 that is exposed is the threaded bore 156 to receive the connecting member of the prosthetic device and establish a connection between the cushioned liner 100 and the prosthetic device.

Suitable techniques for attaching the pin receptacle 150 to the closed distal end 114 include but are not limited to using an adhesive material to bond the pin receptacle 150 to the textile material of the closed distal end 114. It will also be appreciated that a molding process can be used to form the radial skirt portion 152 around the receptacle body 154 and at the same time bond the socket 150 to the distal end 114 of the cushioned sleeve member 100. For example, the receptacle body 154 can be placed into a mold, along with the distal end 114 of the liner body 110 and then polymeric material can be introduced into a mold cavity, thereby forming the radial skirt portion 152 and attaching the pin receptacle 150 to the cushioned liner body 110.

As best shown in the exploded view of FIG. 4, one exemplary liner body 110 is formed of several or more pieces (panels) of textile material that are cut according to an exemplary pattern and then attached to one another along predetermined seams to provide the constructed liner body 110. In one exemplary embodiment, the liner body 110 is formed of three pieces of textile material, namely first and second side panels 160, 170 and a distal panel 180. Preferably, the first and second side panels 160, 170 are identical to one another. Each of the first and second side panels 160, 170 has an upper edge 162 that forms the open end 112 of the liner body 110 when the first and second side panels 160,170 are attached and an opposing lower edge 164 that forms the closed distal end 114 of the liner body 110.

When each of the first and second side panels 160, 170 is flattened out, each panel has a generally rectangular shape with a slight inward taper toward the lower edge 164. In other words, the upper edge 162 has a width slightly greater than the width of the lower edge 164. Each of the first and second side panels 160, 170 has an interior surface 172 (that forms a part of the interior 116 of the liner body 110) and an opposing exterior surface 174 (that forms a part of the exterior 118 of the liner body 110). As best shown in FIG. 4, the first and second side panels 160, 170 are attached to one another along side edges 166 of each. The side edges 166 extend from the lower edge 164 to the upper edge 162.

The distal panel 180 is a textile piece that is cut to have an annular shape or some other desired shape so long as the distal panel 180 encloses one end of the liner body 110 when it is connected to the side panels 160, 170. The distal panel 180 has an interior surface 182, an exterior surface 184 and a peripheral, circumferential edge 186. The dimensions of the distal panel 180 should be such that when the first and second side panels 160, 170 are attached to one another, the distal panel 180 completely extends across the open lower edge (i.e., defined by the lower edges 162 of the panels 160, 170) so as to enclose the distal end (second end 114) of the liner body 110. Accordingly when the first and second side panels 160, 170 are attached to one another along the side edges 166 to form vertical seams, the liner body 110 has a tubular shape and the distal panel 180 is used to enclose the liner body 110. The distal panel 180 is attached to the lower edges 162 of the first and second side panels 160, 170 along its peripheral, circumferential edge 186.

As best shown in FIG. 5, the interior surfaces 172, 182 of the first and second side panels 160, 170 and the distal piece 180, respectively, have a different texture than the exterior surfaces 174, 184. As will be described in greater detail hereinafter, the textile panels 160, 170, 180 are preferably formed of two different materials that are knit together so that the fibers of one material form the exterior surface of the respective piece and the fibers of the other material form the interior surface of the respective piece. The texture of the interior surfaces 172, 182 is designed to absorb the cushioning material that is applied to the interior surfaces 172, 182 to form the cushion layer 120, while not permitting the cushioning material to bleed through or otherwise migrate to the exterior surfaces 174, 184 thereof. As illustrated in FIG. 5, the exemplary interior surface of the textile material has a waffle-like appearance for absorbing the cushioning material.

Referring now to FIGS. 1 through 8, the two side panels of material 160, 170 used to construct the liner body 110 can be attached to one another using any number of conventional techniques, including stitching the two side panels 160, 170 of textile material along the side edges 166 to form vertical stitched seams 171. When the two side panels 160, 170 are stitched to each other, a wide variety of thread types can be used and a number of different stitch types can be used. In one exemplary embodiment, thread formed of a synthetic material, such as nylon, is used to attach the two side panels 160, 170 to one another using a flat-locked stitch. A flat-locked stitch is preferred because this type of stitch tends to create a smooth seam that is less irritating than seams formed of other stitches. A flat-locked stitch also permits the two side panels 160, 170 to sufficiently stretch to accommodate the stretching of the cushioned liner 100 that occurs during the normal wear of the cushioned liner 100.

Similarly, the distal panel 180 of textile material can be connected to the distal lower ends 164 of the two side panels 160, 170 along a circumferential stitched seam 173 using any number of stitch types. However, the distal panel 180 of material is preferably connected to the distal lower ends 164 of the first and second side panels 160, 170 of material using a circumferential seam 173 that has a flat-locked stitch.

The first and second side panels of material 160, 170 and the distal panel 180 can be formed of any number of different textile materials having a predetermined thickness (ply). Preferred textile materials are textile fabrics that have an elasticity that permits the prosthetic liner (cushioned liner 100) to stretch a predetermined amount during normal application of the cushioned liner 100 to the residual limb 130 and during the normal motions of the cushioned liner 100 as the wearer takes steps or otherwise moves the prosthetic limb (i.e., the prosthetic device). For example, the two side panels 160, 170 and the distal panel 180 can be formed of fabrics selected from the group consisting of: stretchable non-woven fabrics (e.g., the Xymide line of fabrics including Wearforce® fabrics from DuPont, Wilmington, Del.); Lycra® based materials which include segmented elastomeric polyurethane fibers (i.e., spandex type fabrics); supplex nylon, neoprene fabrics (polychloroprene fabrics); nylon, spunbonded olefin; looped nylon; spunlaced fabrics; polyester; polypropylene; and aramid fiber fabrics. It will be appreciated that the above list of suitable fabric materials is not exhaustive and is merely exemplary in nature and not limiting of the types of fabric materials that be used to form the liner body 110. Further, it will be appreciated that the fabrics used to form the present liner body 110 are preferably elastic fabrics that can be provided in a woven, knitted, or non-woven form.

One preferred fabric material that is used to form the two side panels 160, 170 and the distal panel 180 is a fabric formed of polyester and polypropylene knit fibers. As shown in FIG. 5, the fabric is constructed (knit) in such a way that the polyester fibers form one surface of the fabric and the polypropylene fibers form the opposite surface of the fabric. In the present prosthetic liner, the polyester surface is intended to form a part of the exterior 118 of the liner body 110, while the polypropylene surface is intended to form a part of the interior 116 of the liner body 110. The polypropylene surface has a distinct texture in that it has a waffle-like texture. When the fibers are knitted in this manner (waffle-like), a number of interstices are formed across the polypropylene surface. As will be described in greater detail hereinafter, the interstitial characteristic of the side of the fabric that forms the interior of liner body 110 advantageously permits gel that is applied to the interior of the liner body 110 to be readily absorbed within the interstices. This type of fabric is commercially available from Milliken & Company of Spartanburg, S.C. under the style/pattern No. 952561-804. Advantageously, a fabric constructed in the aforementioned manner allows the cushioning material to enter into the denure of the fabric but is resistive to the cushioning material migrating through the fabric from the interior surface 116 across the exterior surface 118. In the final product, the cushioning material should be confined to the interior surfaces 116, while the exterior surfaces 118 are free from the cushioning material.

The material used to form the liner body 110 is preferably elastic (stretchable) in one or more, preferably two, directions and is capable of adjusting to variations in form and size of the residual limb 130. Depending upon the precise application, the thickness of the textile material (e.g., fabric) can be altered and while in one embodiment, the material/material thickness of each of the first and second side panels 160, 170 is the same as the material/material thickness of the distal panel 180, it will be appreciated that the material and/or material thickness of any one of the first and second side panels 160, 170 and the distal panel 180 can be different from the other pieces. In one exemplary embodiment, the thickness of the fabric material used to construct the liner body 110 is from about 0.010 inch to about 0.200 inch. In the embodiment where the fabric material is a knit of polyester and polypropylene fibers, the thickness of the fabric material is about 0.04 inch; however, the thickness of the polyester/polypropylene knit can vary depending upon the particular application.

Figure 9:
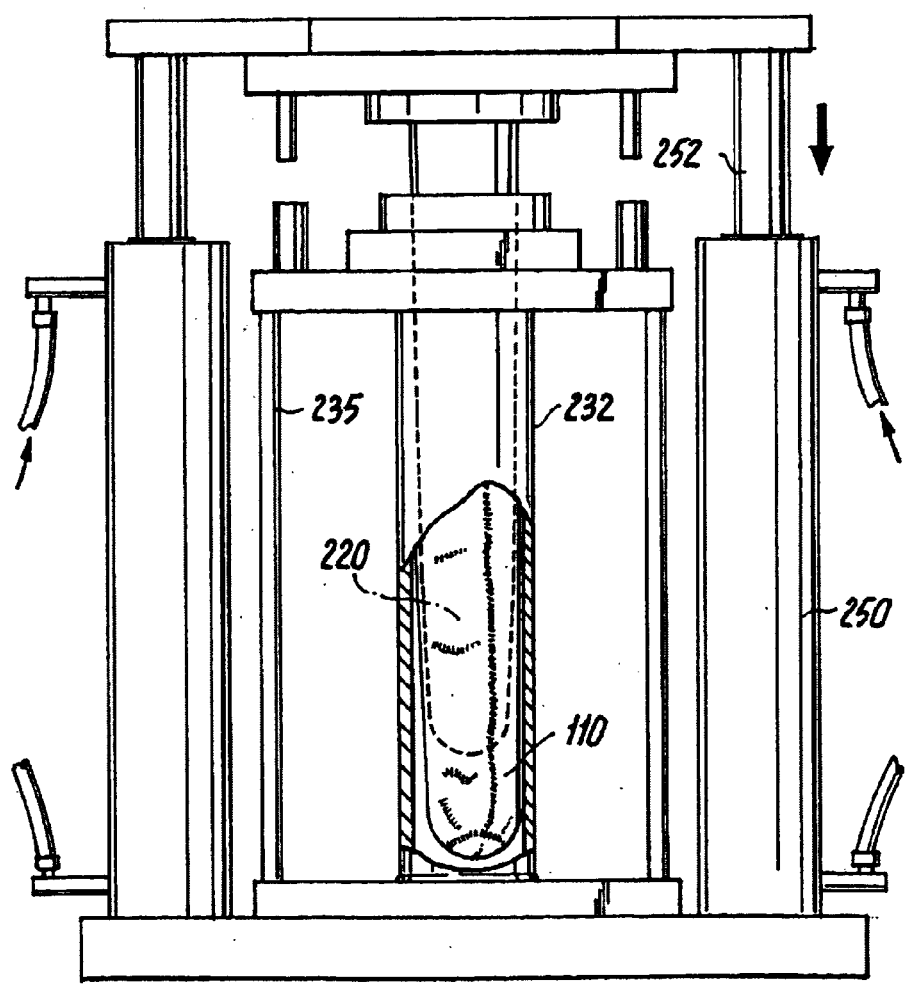
FIG. 9 is a side elevational view, in partial cross-section, of the apparatus of FIG. 7 illustrating a mandrel being extended to an intermediate position inside of the liner body.
Figure 10:
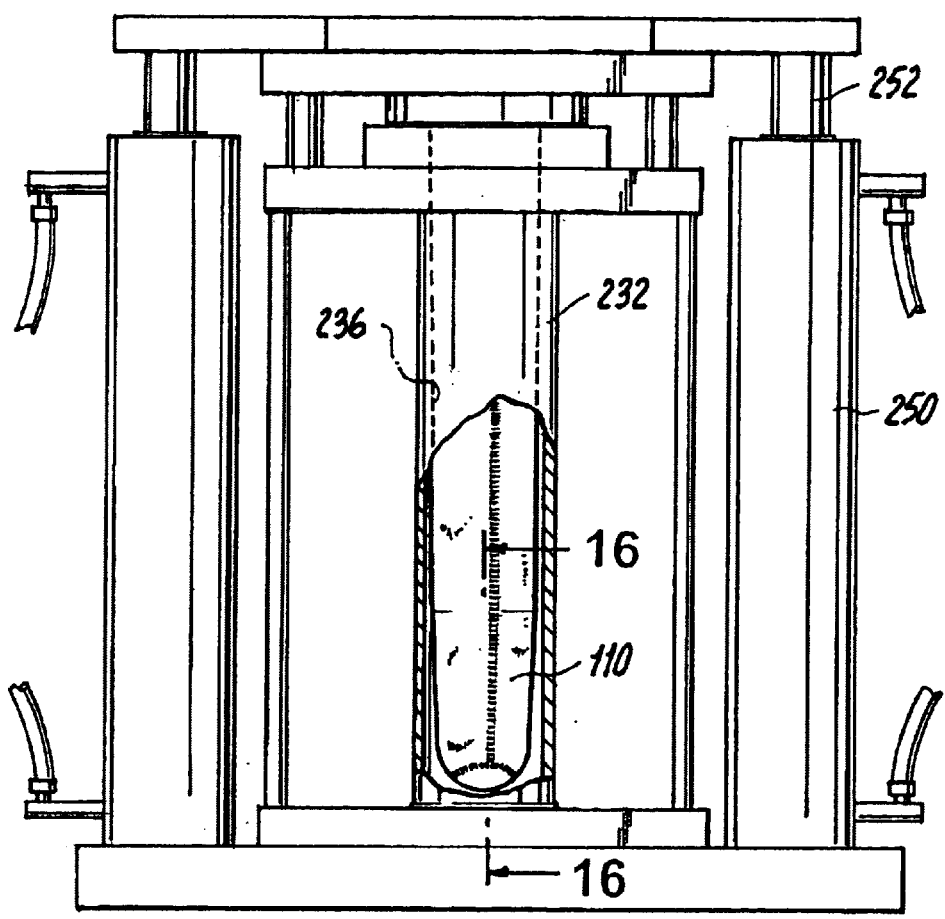
FIG. 10 is a side elevation view, in partial cross-section, of the apparatus of FIG. 9 illustrating the mandrel being further extended to a distal position.
Figure 11:
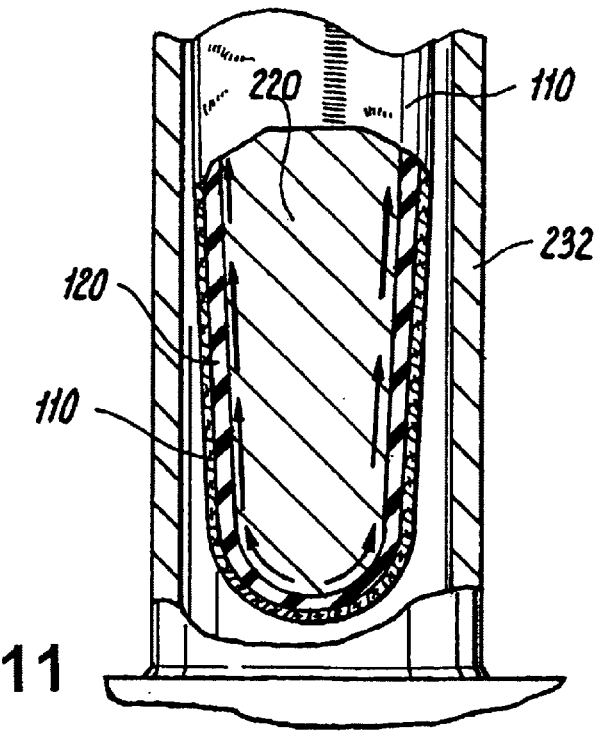
FIG. 11 is an enlarged cross-sectional view of the mandrel in the distal position of FIG. 10 with cushioning material flowing around the mandrel between the mandrel and the inside surface of the liner body.

As best shown in FIGS. 9 through 11, the cushioned liner 100 of FIGS. 9 and 10 provides a number of advantages over conventional prosthetic liner. More specifically, the distal seam of the traditional prosthetic liner 10 has been eliminated by constructing the present cushioned liner 100 so that it includes a distal panel 180 at the distal end 114 that is attached to the two side fabric panels 160, 170 along the circumferential seam 173 that extends around the peripheral edge of the distal panel 180 instead of being formed across a medial section as in the traditional prosthetic liner 10. By eliminating a distal seam that extends across the distal end of the prosthetic liner, such as a conventional distal seam the wearer of the present cushioned liner 100 experiences increased comfort since the conventional distal seam is associated with irritation and general discomfort, even in the cases when the conventional distal seam is covered with a cushioning material.

It will be appreciated that the distal end 114 of the cushioned liner 100 does not include a seam that is positioned in a location where the residual limb 130 will come into contact therewith. In many cases, the residual limb 130 tapers inwardly toward its distal stump end due to the natural shape of a leg and as a result of typical surgical techniques that are employed during an amputation procedure. The residual limb 130 thus rests against the cushion layer 120 in an area that is within the circumferential seam 173 or at least preferably contacts the circumferential seam 173 at the most peripheral portions of the residual limb 130. At the very least, the wearer of the present cushioned liner 100 does not experience a distal seam running across underneath the residual limb 130 and preferably, the cushioned liner 100 is constructed so that the contact between the residual limb 130 and the circumferential seam 173 is negligible or nonexistent. As previously-mentioned, this distal end of the residual limb 130 is an extremely sensitive area and therefore, the elimination of any stitching across this sensitive area, provides a cushioned sleeve member that is substantially more comfortable than traditional prosthetic liners.

The cushioning material is applied to the interior surfaces 172, 182 of the first and second side panels 160, 170 and the distal panel 180, respectively, to form the cushion layer 120. The process of applying the cushioning material and controlling the thickness of the cushioning material, so as to permit contouring of the cushioning material, along the interior surface 116 of the liner body 110, will be described in greater detail below. Preferably, the cushioning material is applied to interior surfaces 172 of the first and second side fabric panels 160, 170 to coat these panels from the lower edge 164 to the upper edge 162 and is also applied to the interior surface 182 of the distal panel 180.

As previously-mentioned, the cushioned liner 100 includes the layer 120 of cushioning material and has a form fitting shape with an open end 112 into which the amputation stump 130 may be introduced, a closed end opposite the open end, an interior and an exterior. The interior of the cushioned liner 100 is defined by the interior surfaces 172, 182 of the panels 160, 170, 180 that are attached to one another and the interior surfaces 172, 182 are impregnated with a cushioning material to provide a cushion (e.g., cushion layer 120) between the amputee's residuum 130 and any prosthetic device to be worn, attached to, etc., the residuum 130.

The cushioning material is preferably a polymeric material and in one exemplary embodiment, the cushioning material is formed of a gel, a thermoplastic elastomer, or a combination thereof. For example, suitable thermoplastic elastomers include but are not limited to thermoplastic rubbers, silicon containing elastomers, thermoformable materials, etc., that provide a comfortable interface between the residuum 130 and a prosthetic device.

In one exemplary embodiment, the cushioning material is a polymeric gel that is composed of a block copolymer and mineral oil. The gel that can be used to form the cushioning material can either be a nonfoamed gel or a foamed gel (which is produced using a foaming agent). The mineral oil is present in an amount that is effective to produce a cushioning material having desired properties and is preferably present in from 0–85% by weight based on total weight, depending upon the precise application.

The polymeric material used to form the cushioned liner 100 is characterized by a certain durometer range. According to one exemplary embodiment, durometers for the cushioning material range from 1–20 on the Shore "A" scale. The lower the Shore A number, the softer the material, typically due to a higher level of plasticizer. Preferably the polymeric gel has a durometer (Shore A) that matches or approximates human skin and it has been found that the above durometer range of 1–20 generally provides the gel material with suitable characteristics. In one embodiment, the mineral oil is present on an equal weight basis, or in a weight ratio of 1/4, with regard to the amount of polymeric material present. The mineral oil is preferably purified mineral oil and is preferably USP grade.

In one exemplary embodiment, the cushioning material is formed of a Kraton®-type rubber material (Shell Chemical Co.). For example, the polymeric material can be formed of the following Kraton® rubbers: styrene-ethylene/butylene-styrene block copolymers or styrene-ethylene/propylene block copolymers and are available in triblock and diblock form.

The polymeric cushioning material can also be a blend of Kraton® rubbers and oils, such as mineral oils, (including typical stabilizers) which provide an average durometer of from 1–20. These blends typically are formed of a rubber having a lower durometer (1–10 of the Shore "A" scale) and a rubber having a higher durometer (e.g., 11–20). The blends are preferably capable of being stretched 100% or more before tearing and are capable of providing a form fit to the residual limb due to their inherent elasticity. Further, low durometer Kraton® rubbers and other materials tend to provide the cushioning material disposed of the interior 116 of the cushioned liner 100 with a sticky feeling which enhances the ability of the cushioned liner 100 to be form fitted against the residual limb 130 due to the intimate contact between the cushioning material and the skin.

In one exemplary embodiment, the polymeric material is a styrene isoprene/butadiene block copolymer or styreneethylene/butadiene-styrene block copolymer. Suitable polymeric materials, having the aforementioned desired properties, are commercially available from a number of sources. For example, polymeric materials commercially distributed under the trade names C-Flex 1970-W5 (R70–339–000), C-Flex 1960-W5 by Consolidated Polymer Technologies of Largo, Fla. and under the trade name Kraton G1654 by Shell Chemical Co. are suitable for use in producing the cushioning material.

The ratio of polymer to mineral oil will vary depending upon the precise application and upon the desired characteristics of the cushioned liner 100. Generally, the ratio of polymer to mineral oil can be from about 1:1 to about 4:1. In addition to using styreneisoprene/butadiene or styrene-ethylene/butadiene-styrene block copolymers (mixed with mineral oil), other suitable polymeric materials include styrene-butadiene-styrene and any thermoplastic elastomer or thermoformable material that is capable of being blended with mineral oil and can perform the prescribed function of providing a cushioning material suitable for use in the intended applications. Mixtures of all of the aforementioned polymers can also be used to form the polymeric cushioning material.

In one preferred exemplary embodiment, the cushioning material is a polymeric material that has gel-like characteristics and is formulated as a blend of a polystyrene-poly(ethylene-ethylene/propylene)-polystyrene block copolymer (SEEPS) and oil, such as one or more mineral oils. A suitable gel-like cushioning material formed of a SEEPS copolymer/mineral oil blend is commercially available under the trade name PolyGel 51299 from PolyGel LLC of Whippany, N.J.

The cushioning material is also selected so that the cushioned liner 100 can be placed on the residual limb 130 in such away that the polymeric material does not drag against the skin. For example, it is desirable for the cushioned liner 100 to be capable of being rolled before the cushioned liner 100 is placed on the residual limb 130 and/or prosthetic device. Advantageously, the cushioning material is also designed to provide beneficial moisture to the residual limb 130 during the wearing of the cushioned liner 100. Moreover, the cushioning material may include antioxidants, such as vitamins A, B, and C or any other antioxidants commonly used in polymers. In addition, skin conditioning agents can be added to the polymeric material of the cushioned liner 100 to soothe the skin of the residuum during wear. Such skin conditioners include mineral oil, baby oil, etc., which can be added to the polymeric material prior to its application to the sleeve member. Also, astringents, biocides, medicaments, etc., can be added or applied to the cushioning material to avoid infection or heal sores, etc.

The size of the cushioned liner 100 can be varied depending upon the dimensions of the residual limb to be enclosed by simply proportionally varying the dimensions of the pattern which is used to cut and form each of the first and second side panels 160, 170 and the distal panel 180. In other words, the length of the cushioned liner 100 of any of the embodiments disclosed herein can vary and the cushioned liner 100 can easily be manufactured in a number of different sizes by simply altering the dimensions of the patterns used to form the first and second fabric side panels 160, 170 and the distal piece 180. In one exemplary embodiment, the cushioned liner 100 has a length between about 8 inch to about 20 inch. Typically, the cushioned liner 100 is constructed to have a prescribed length and then the individual wearer's can modify the length of the cushioned liner 100 by simply cutting and removing an upper portion of the article. In this manner, the cushioned liner 100 can be initially produced to have a length that fits or can be easily modified to fit a large percentage of the potential customers.

As will be described in great detail hereinafter, the thickness of the cushioning material can vary along the interior surfaces 172, 182 of the first and second side fabric panels 160, 170 and the distal panel 180, thereby permitting thickness variations in prescribed areas where additional cushioning is desired to provide added comfort and protection or where less cushioning is desired due to other practical considerations. The overall thickness of the cushioned liner 100, that is the sum of the thicknesses of the textile liner body 110 and the thickness of the cushion layer 120, is between about 2 mm and 19 mm, according to one exemplary embodiment. It will be understood that the foregoing measurements are merely illustrative and do not limit the scope of protection for the cushioned liner 100. Thus, there may be particular applications where a thickness outside of the aforementioned range may be desired.

One exemplary process of applying the cushioning material to an article, such as the liner body 110, is illustrated in FIGS. 7 through 15. For purpose of illustration only, the present process will first be described with reference to the exemplary liner body 110; however, it will be understood that any type of liner article can be used in place of the liner body 110. In other words, conventional articles, including conventional liners can be used in the present process.

In this embodiment, the cushioning material is applied under pressure and is done in such a way that the thickness of the cushioning material can be controlled to a much greater degree of precision compared to conventional methods of applying the cushioning material, including the aforementioned dipping process. The thickness of the cushioning material can also be varied in select regions of the liner body so as to provide additional or less cushioning in the selected regions.

An apparatus 200 for applying the cushioning material under pressure to the interior 116 of the liner body 110 is illustrated in FIG. 7. The apparatus 200 includes a base member 210 and a positionable mandrel 220. The base member 210 has a cavity 230 formed therein and has a predetermined shape and predetermined dimensions that can be varied according to the precise application. The base member 210 has an upper surface 212 that is preferably planar in nature and the cavity 230 is defined by a surrounding structure 232, which in the illustrated embodiment is a vertical housing that has a circumferential outer surface 234 and an inner surface 236 (cavity wall) that defines the cavity 230. The vertical housing 232 thus has an open end 231 and an opposing closed second 233.

In the exemplary embodiment, the base member 210 includes a first plate 227 which defines the upper surface 212 and a spaced second plate 229 with a number of legs 235 extending between the first and second plates 227, 229 to support the first plate 227 relative to the second plate 229. The vertical housing 232 extends between the first and second plates 227, 229 and can extend through complementary openings formed in one or more of the first and second plates 227, 229. The vertical housing 232 preferably is arranged in a central location of both of the first and second plates 227, 229 such that the legs 235 are located radially around the vertical housing 232. It will be understood that a number of different constructions are possible for the base member 210 so long as the base member 210 includes the cavity 230. The base member 210 can be formed of a number of materials so long as the material that defines the cavity 230 can be exposed to the elevated temperatures that are required to produce liquid or molten cushioning material without being damaged or otherwise impaired. Preferably, the base member 210 is formed of a metal material.

Optionally, the cavity 230 is communicatively connected to a vacuum source (not shown) such that the cavity 230 can be placed under a vacuum at select times during the process for applying the cushioning material to the liner body 110. For example, a vacuum is preferably applied near or at the distal, closed end 233 of the cavity 230 to provide a force to assist the placement of the liner body 110 within the cavity 230. More specifically, one or more vacuum ports (not shown) are formed in the vertical housing 232 and in communication with the cavity 230 at or near the distal closed end 233 thereof. A conduit (e.g., tubing) can connect the vacuum ports to the vacuum source. When the vacuum source is actuated, air is withdrawn through the vacuum ports, thereby resulting in a pressure reduction in the distal end of the cavity 230. As will be described hereinafter, the liner body 110 is inserted into the cavity 230 such that the closed end 114 of the liner body 110 is inserted first and is positioned near or at the closed end 233 of the cavity 230. Because it is desirable to open up the liner body 110 so that it assumes a more tube-like shape, the actuation of the vacuum source causes the fabric material of the liner body 110 to be pulled toward the cavity wall of the cavity 230. The vacuum source thus serves to properly locate the liner body 110 within the cavity 230 (i.e., position and retain the closed distal end 114 of the sleeve member 110 at the closed end 233 of the cavity 230).

The mandrel 220 is an elongated structure having a first end 221 and a second end 222 that is received within the cavity 230 during the process of applying the cushion material to the interior 116 of the liner body 110. The exemplary mandrel 220 thus has a complementary shape relative to the cavity 230 so that at least a predetermined length of the mandrel 220 can be inserted into the cavity 230. In one exemplary embodiment, the mandrel 220 has a generally annular cross-sectional shape with the second end 222 terminating in a smooth rounded portion.

The cross-sectional dimensions of the mandrel 220 are preferably not uniform from the first end 221 to the second end 222. More specifically, the width of the mandrel 220 preferably varies along its length such that the mandrel 220 has a greater width near the first end 221 than at the second end 222. The mandrel 220 can thus be thought of as having an inward taper from the first end 221 towards the second end 222. While a number of different materials can be used to form the mandrel 220, the mandrel 220 must be formed of a material that can withstand the elevated temperatures of the liquid or molten cushioning material (e.g., 300°–400°). In one exemplary embodiment, the mandrel 220 is formed of a metal material.

The first end 221 of the mandrel 220 is connected to a base 223 that in turn can be connected to a larger sized support platform 225 that is preferably dimensioned so that it extends across the first plate 227.

The mandrel 220 is part of a system that includes a controller for adjusting the position of the mandrel 220 relative to the cavity 230. In one exemplary embodiment, the mandrel 220 is pneumatically operated by a programmable control unit that adjusts the position of the mandrel 220. In this embodiment, a pair of pneumatic cylinders 250 with drivable pistons 252 are disposed around the vertical housing 232 that includes the cavity 230. First ends of the pistons 252 are connected to the support platform 225 such that when the pistons 252 are pneumatically driven, the pistons are either extended or retracted within the cylinders 250, thereby causing relative movement of the support platform 225 and the mandrel 220 which is attached thereto. Because the mandrel 220 is axially aligned with the open end 231 of the cavity 230, the retraction of the pistons 252 causes the mandrel 220 to be drawn into the cavity 230.

Since the complete system is preferably a programmable computer controlled system, the precise coordinates of the mandrel 220 can easily be determined and monitored. Accordingly, the position of the mandrel 220 within the cavity 230 can be monitored.

Figure 8:
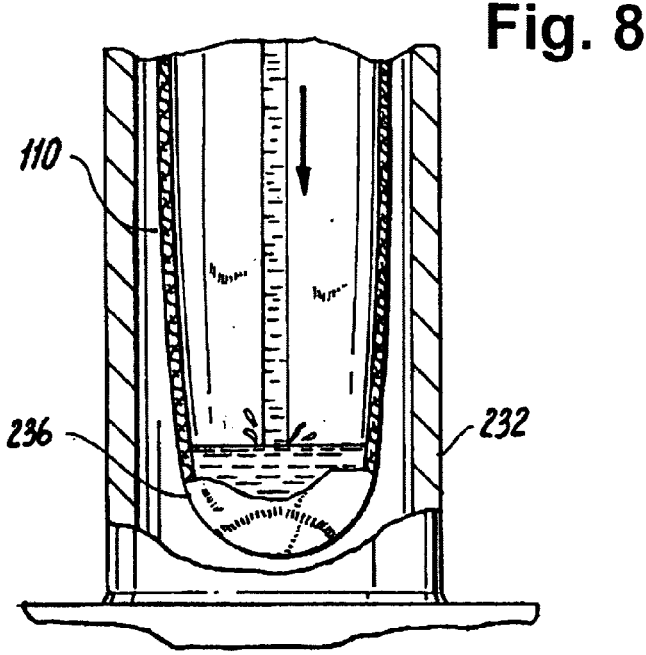
FIG. 8 is an enlarged cross-sectional view illustrating a housing member having a cavity for receiving the liner body which in turn receives liquid or molten cushioning material.

Referring to FIG. 8, the interior 116 of the liner body 110 is coated with the cushioning material in the following manner which ensures that the thickness of the cushioning material can be controlled with increase precision compared to conventional techniques. The liner body 110 is placed into the cavity 230 with the distal closed end 114 being inserted first into the cavity 230 and the liner body 110 is then properly located within the cavity, preferably by actuating the vacuum source to cause the liner body 110 to be drawn towards the cavity wall 236 of the cavity 230. In this manner, the liner body 110 assumes a more tube-like shape with the side panels 160, 170 be drawn apart from one another.

The cushioning material is heated to an elevated temperature that is above the point at which the cushioning material turns to a liquid or molten state and then the liquid or molten cushioning material is introduced into the inside of the liner body 110 by any number of conventional techniques, including injecting or otherwise feeding the cushioning material into the liner body 110. As previously-mentioned, the entire system is preferably a programmable, computer controlled system which is capable of determining the amount of cushioning material that needs to be introduced into the liner body 110 in order to provide a cushioning layer 120 having a predetermined thickness. The amount of cushioning material that is introduced is determined based upon a number of factors including but not limited to, the dimensions of the sleeve member 110, the dimensions of the mandrel 220, the dimensions of the cavity 230, etc.

As the cushioning material is added, it will pool within the inside of the liner body 110 at the closed distal end 114 thereof as best shown in FIG. 8. The fabric material forming the liner body 110 is impermeable to the cushioning material and therefore, the cushioning material does not migrate from the interior 116 to the exterior 118. In order to effectively coat the inside of the liner body 110 to a predetermined thickness, the mandrel 220 is introduced inside of the liner body 110 (FIG. 9). The mandrel 220 is directed within the inside of the liner body 110 to a predetermined position where the distal end 222 of the mandrel 220 is disposed proximate to the closed distal end 114 of the liner body 110 (i.e., the distal end 222 is spaced a predetermined distance from the closed distal end 114). It will be appreciated that as the mandrel 220 is moved into this preselected position, the distal end 222 contacts the pool of cushioning material and as the mandrel 220 is further driven towards the closed distal end 114, the motion of the mandrel 220 causes the cushioning material to flow around the mandrel 220 as illustrated in FIGS. 10 and 11. In effect, the cushioning material is forced up the sides of the mandrel 220 between the mandrel 220 and the inside surface of the liner body 110. By carefully controlling the distance between the outer surface of the mandrel 220 and the interior surface of the liner body 110, the precise thickness of the cushioning layer 120 can be controlled. In other words, the thickness of the cushioning layer 120 will necessarily be the distance between the outer surface of the mandrel 220 and the interior surface of the liner body 110. However, the cushion material is slightly overpoured into the liner body 110 to ensure that a sufficient amount of cushion material is present to form the desired thickness of cushion layer 120.

The amount of cushioning material that is introduced into the inside of the liner body 110 is preferably determined beforehand so that cushioning material is not wasted when the mandrel 220 is introduced into the liner body 110 to cause the cushioning material to be dispersed around the mandrel 220. For example, if an excessive amount of cushioning material is disposed within the liner body 110, the action of the mandrel will cause the cushioning material to be discharged from the cavity 230 since there is an excessive amount of cushioning material to fit within the space between the outer surface of the mandrel 220 and the interior of the liner body 110.

The mandrel 220 can optionally include an extra safeguard to prevent the cushioning material from being discharged from the cavity 230. For example, the mandrel 220 can include a movable sleeve (not shown) at or near the end 221 of the mandrel 220 that is positionable between a retracted position and an extended position where the sleeve covers the gap between the mandrel and the interior surface of the liner body 110. In one exemplary embodiment, the movable sleeve is a spring-loaded ring that surrounds the mandrel 220 and is biased against the interior surface of the liner body 110. The spring-loaded ring serves to prevent the cushioning material from flowing out of the cavity 230 since it extends across and seals off the passage where the cushioning material flows.

Figure 13:
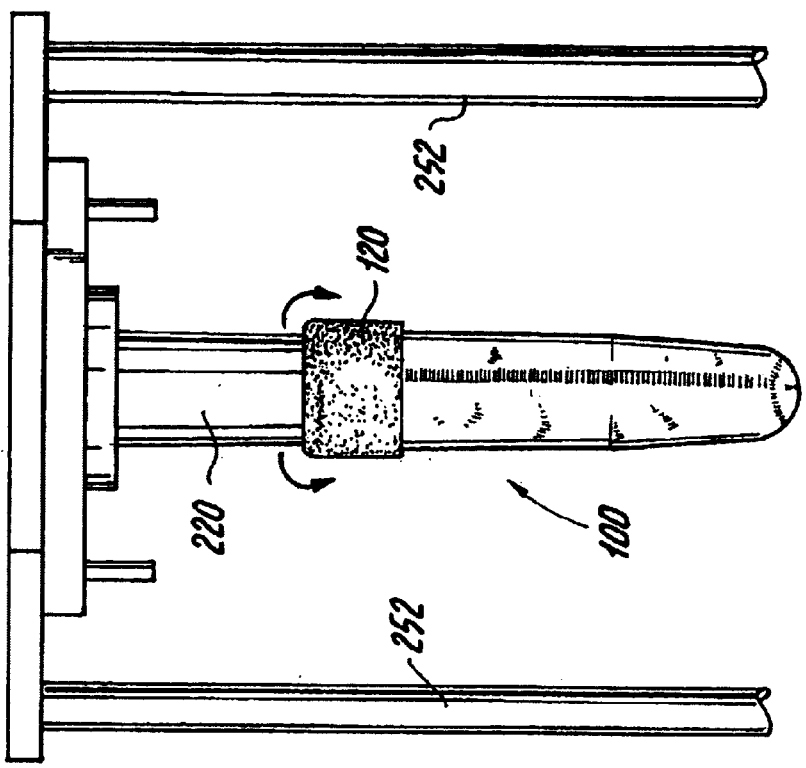
FIG. 13 is a side elevation view of the mandrel in the retracted position of FIG. 12 with the cushioned liner being rolled or peeled therefrom for removal of the cushioned liner.
Figure 12:
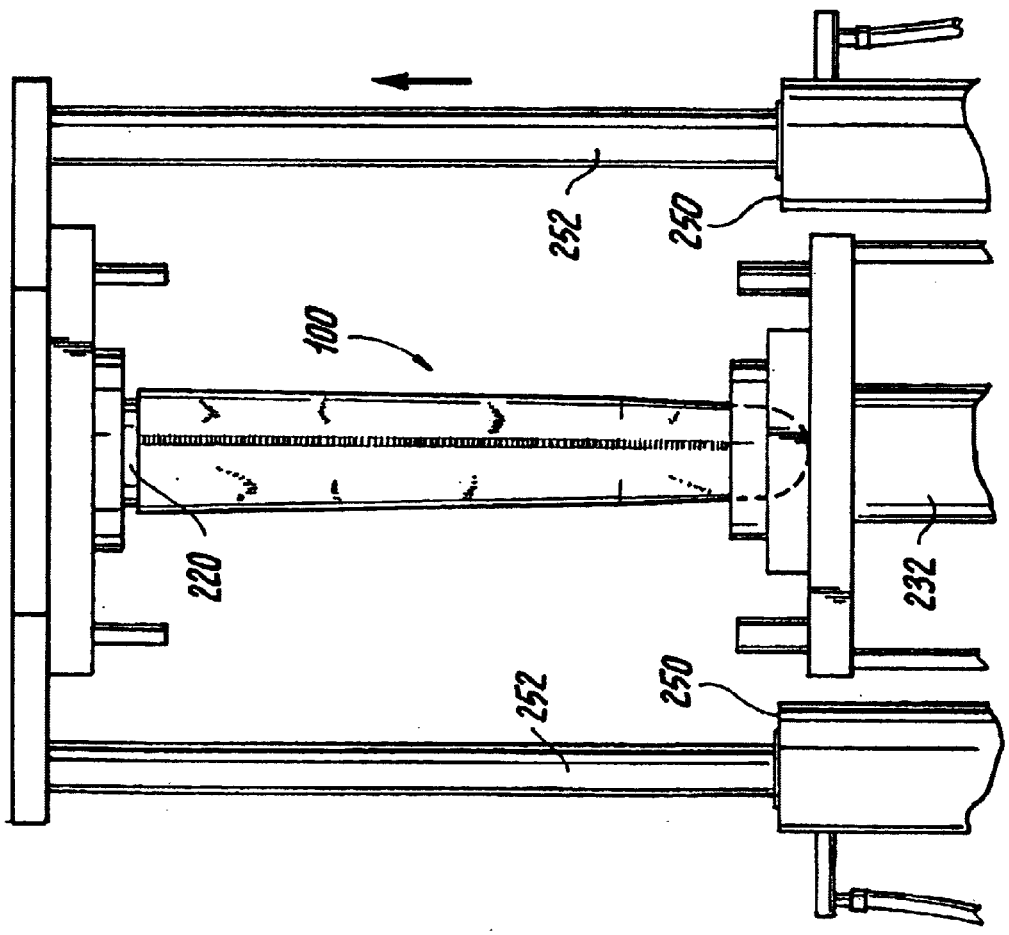
FIG. 12 is a side elevational view of the apparatus of FIG. 7 illustrating the mandrel being retracted from the cavity with the cushioned liner of FIG. 1 surrounding the mandrel.

Once the mandrel 220 is driven to the preselected extended position to cause the cushioning material to flow around the mandrel 220, the cushioning material is permitted to cool for a predetermined amount of time. This results in the cushioning material solidifying into the gel-like cushion layer 120. After the cooling period has passed, the mandrel 220 is retracted from the cavity 230 with the cushioned liner 100 still being disposed over the mandrel 220 as illustrated in FIG. 12. The cushioned liner 100 is then removed from the mandrel 220 by rolling the cushioned liner 100 off of the mandrel 220 as illustrated in FIG. 13.

It will be appreciated that the application of a vacuum within the cavity 230 is not critical as it merely assists opening the liner body 110. This process of applying the cushioning material offers a number of advantages over conventional methods since it provides a simple yet effective process for controlling the thickness of the cushion layer 120 to a greater degree of precision compared to conventional techniques. Because the distance between the mandrel 220 and the interior of the liner body 110 can be determined for any point along the mandrel 220 and the liner body 110, the thickness of the cushion layer 120 is controlled since the thickness is defined by the distance between the mandrel 220 and the interior 116 of the liner body 110 when the exterior 118 of the liner body 110 is against the cavity wall 236 of the cavity 230.

Figure 15:
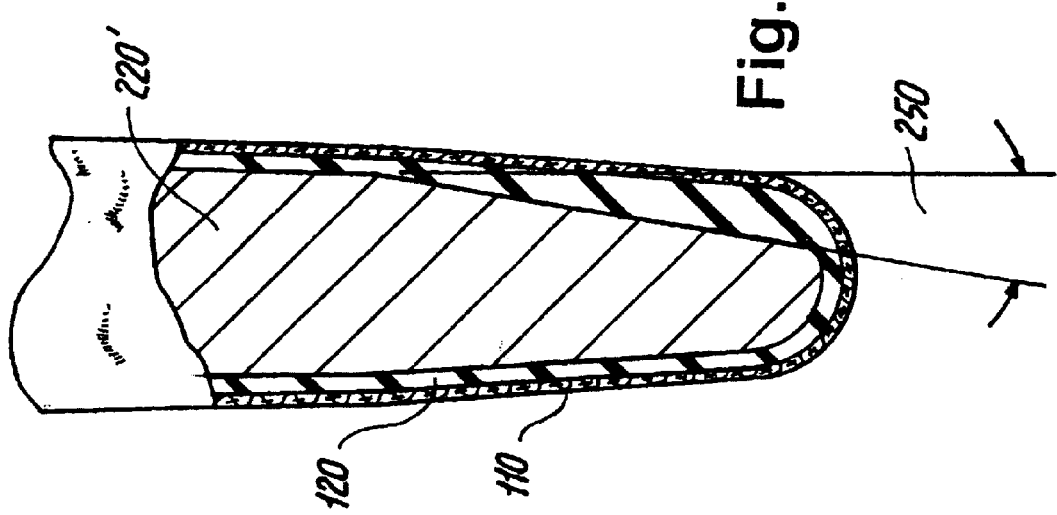
FIG. 15 is an enlarged cross-sectional view illustrating the mandrel of FIG. 14 being inserted into a liner to form a cushion layer having a section of increased thickness.
Figure 14:
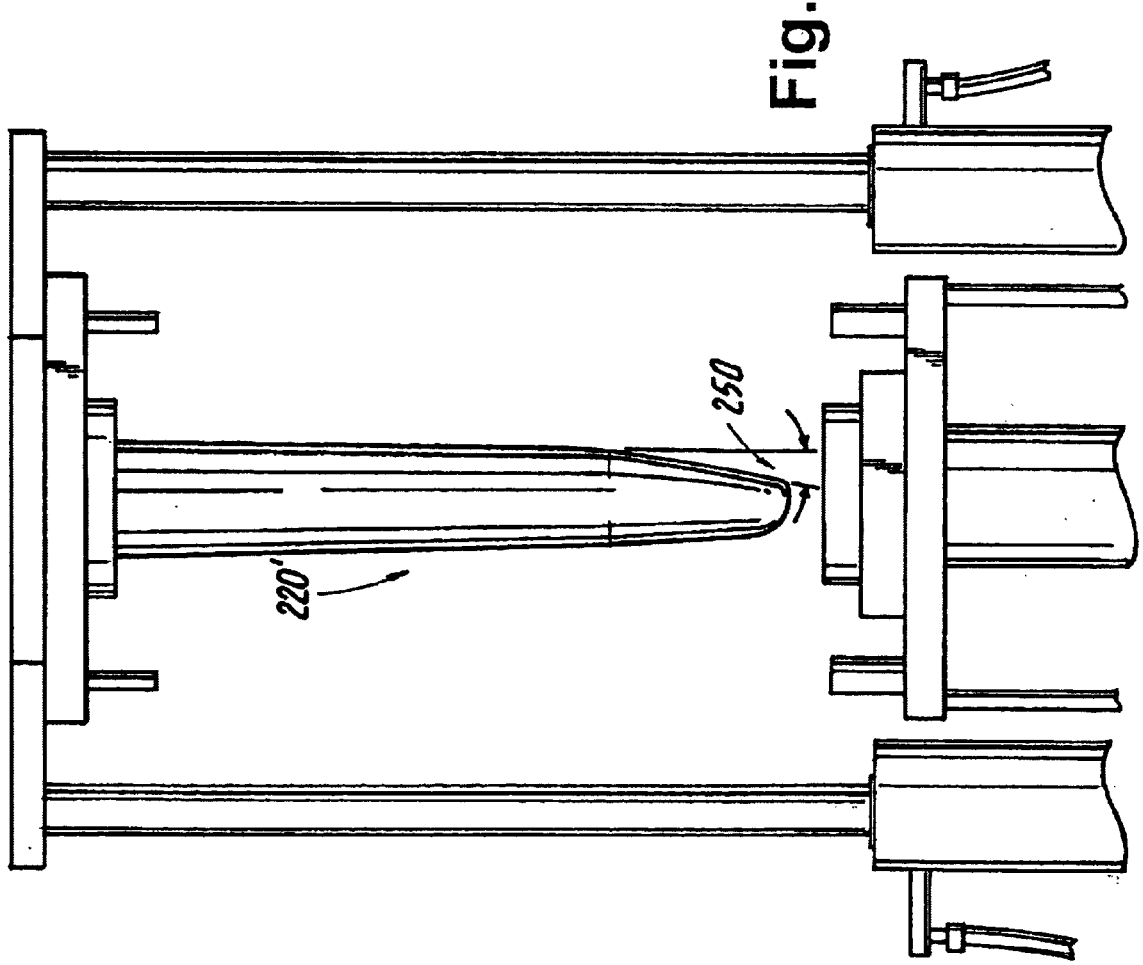
FIG. 14 is side elevational view of an apparatus according to an alternative embodiment for applying a cushioning material to a liner body to form the cushioned liner of FIG. 1, wherein the mandrel is formed to have a non-uniform shape.

Referring to FIGS. 14 and 15, it will also be appreciated that the inside contour of the cushion layer 120 (i.e., the interior 116 of the cushioned liner 100) is controlled by the contour of one or more of the mandrel 220 and the cavity 230. In one embodiment, the mandrel 220 is customized for a given application by altering the shape of the mandrel 220 along its longitudinal axis. For example, the mandrel 220 can include a recessed section along its length and when the mandrel 220 is introduced into the cavity 230 and the cushion material flows around the mandrel 220, the cushion material will settle within the recessed section of the mandrel 220. Because the distance between the recessed section and the liner body 110 is greater than the distance between surrounding portions of the mandrel 220 and the liner body 110, the thickness of the cushion layer 120 is greater in this section. Thus, a localized area of the interior 116 of the liner body 110 is formed to a greater thickness than surrounding sections. Preferably, this localized area of increased thickness is formed in an area where extra cushion is desired to provide additional comfort to the wearer as is the case in some of the sensitive interface locations between the residual limb 130 and the prosthetic device, etc. For example, the front portion of the cushioned liner 100 and distal end 114 are regions where additional comfort is desired since these regions (i.e., the shin area and distal stump area) correspond to sensitive areas of the residual limb 130. The amount of cushion material at the distal end 114 is controlled by the distal shape of the mandrel 220 and by the final position of the mandrel 220 relative to the distal end 114 of the liner body 110 (i.e., the greater the distance between the mandrel and the distal end 114, the greater the thickness of the cushion layer 120).

It will be appreciated that the mandrel 220 can be contoured in any number of different ways depending upon the desired contour of the cushion layer 120 of the cushioned liner 100. For example, the inward taper of the mandrel 220 can be non-uniform in manner to produce variations in thickness along the interior 116 of the cushioned liner 100. This embodiment is generally shown in FIGS. 14 and 15 in which a mandrel 220' is illustrated. The mandrel 220' is similar to the mandrel 220 with the exception that the distal end portion of the mandrel 220' has a non-uniform cross-sectional shape. More specifically, one section of the distal end portion has a pronounced taper 250. In this section having a pronounced taper 250, the distance between the mandrel 220 and the liner body 110 is greater than in other surrounding sections and therefore, additional cushioning material is permitted to flow and ultimately cool and form the cushion layer 120 in this area. FIG. 15 clearly shows that the incorporation of the pronounced taper 250 into the mandrel 220 results in the cushioned liner 100 having one section (e.g., a front shin portion thereof) that has additional cushioning material provided thereat so as to provide the wearer with added comfort and protection in this sensitive area.

It will be appreciated that the mandrel 220 can be modified in any number of different ways to selectively control the thickness in localized areas of the cushioned liner 100. For example, the distal end 222 of the mandrel 220 can have an annular recessed section that receives additional cushioning material, thereby altering the thickness profile at the distal end 114 of the cushioned liner 100.

If an area of reduced thickness is desired, the mandrel 220 can be modified to include one or more protruding features (i.e., a section of the outer surface of the mandrel 220 that protrudes outwardly relative to the surrounding sections of the mandrel 220). Each protruding feature reduces the distance between the mandrel 220 and the interior of the liner body 110 and thus causes the cushion layer 120 to have a reduced thickness in this region.

In another aspect, the cavity 230 does not necessarily have to have a uniform shape; but rather, the cavity 230 can be formed to have any number of shapes. By altering the contour of the cavity 230, the thickness of the cushion layer 120 of the cushioned liner 100 can be varied in select locations. For example, the cavity wall of the cavity 230 can include a recessed section or a protruding section to cause the liner body 110 assume a different shape in this section.

Thus, it will be understood that the present process permits a number of different cushioned liners 100 to be produced using a limited amount of equipment since the mandrel 220 is interchangeable and one mandrel 220 having one profile can be interchanged for another mandrel 220 having another profile. By interchanging the mandrel 220 and maintaining the same cavity 230, the thickness and contour of the cushion layer 120 can be controlled to a high degree of precision. Further, the present process is less complicated than the conventional methods, including the dipping method, as it does not require a series of steps to build-up the cushion layer 120 to the desired thickness nor does it require that the cushioned liner 100 be inverted after the cushion layer 120 is formed on the interior of the liner body 110.

The present process of using compression molding techniques to apply a cushion layer to the liner body is not limited to being merely used to produce cushioned liners (i.e., prosthetic liners) but rather, the present process can be used to produce other articles, including cushion or gel products that do not contain a fabric component and also other products, such as cushioning pads that can be incorporated into socks and other products to be worn on one of the various limbs of the body, i.e., an elbow pad. The cushioned pad products can include a fabric layer (liner) on one side or both sides.

In another embodiment, a cushion article (i.e., a pad) (not shown) is formed without a fabric backing layer (i.e., liner body 110). In other words, the article is formed entirely of cushioning material that is molded to have a predetermined, desired shape. The article is preferably formed using the apparatus shown in FIGS. 7–15. In this embodiment, the liner body 110 is not introduced into the apparatus 200 and more specifically, the cushioning material is disposed in the cavity 230 such that the cushioning material pools at the closed distal end of the cavity 230. The mandrel 220 is then introduced into the cavity 230 and driven towards the distal end 233 of the cavity 230. As the mandrel 220 is driven to its fully extended position, it compresses the pool of cushioning material, causing the cushioning material to flow around the outer surface of the mandrel 220. As previously-described in detail, the thickness of the article is controlled by the distance between the mandrel 220 and the wall 236 of the cavity 230. Because this distance can be carefully and precisely controlled, the thickness of the article can likewise be precisely controlled.

The article is thus formed between the outer surface of the mandrel 220 and the wall 236 of the cavity 230. After the cushioning material has been sufficiently cooled, the mandrel 220 is retracted from the cavity 230 with the article still being coupled to (i.e., surrounding) mandrel 220. The article is then rolled or otherwise removed from the mandrel 220. The article can be formed to have any number of shapes and sizes by varying the size and shape of at least one of the mandrel 220 and the cavity 230. For example, article can be constructed to act as a resilient cushioning member that can be fitted around a toe or finger.

Now referring to FIGS. 16–23, FIG. 16 shows another exemplary article 400 that can be formed using the compression molding process disclosed herein. In this embodiment, an apparatus 500 is used to form the article 400. The apparatus 500 shares some similarities with the apparatus 200. The apparatus 500 includes a mold body 510 having a recessed mold cavity 512 for receiving the cushioning material and optionally, one or more fabric layers. The apparatus 500 also includes a positionable mandrel plate 520 for dispersing the cushioning material under compression across the cavity 512 so that the cushioning material spreads across the cavity 512 and is formed to a predetermined thickness. In this embodiment, the mandrel plate 520 has a recessed portion 522 that receives the liquid or molten cushioning material and at least partially defines the shape of the article 400. As shown in FIG. 18, the mandrel plate 520 fits intimately within the cavity 512 such that a peripheral edge of the mandrel plate 520 seats against the cavity floor and the cushioning material is forced into the recessed portion 522.

After the cushioning material has sufficiently cooled, the mandrel plate 520 is retracted and the article 400 is removed from the recessed section 522 as illustrated in FIG. 19.

Figure 20:
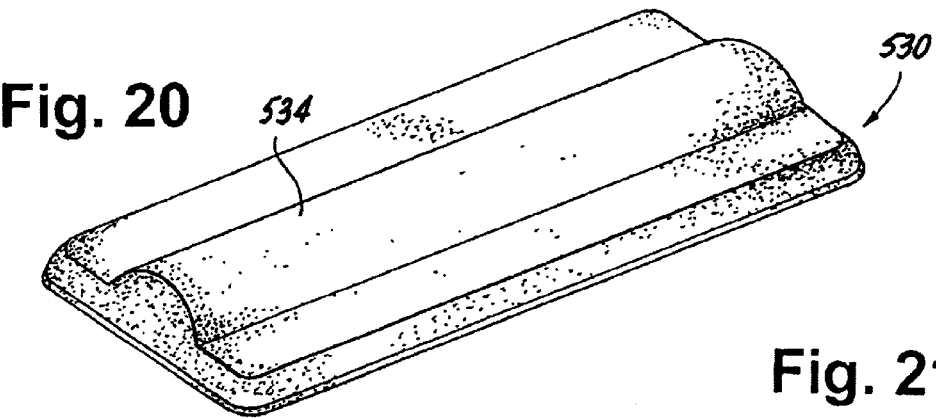
FIG. 20 is a perspective view of an alternative cushioned article having a surface feature.
Figure 21:
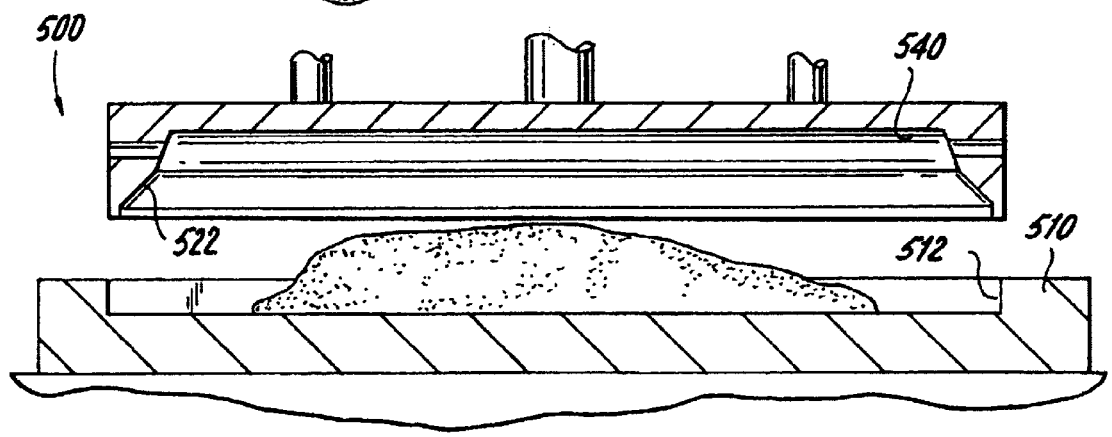
FIG. 21 is a cross-sectional side elevational view of an exemplary apparatus for forming the article of FIG. 20 with a mandrel being shown in the retracted position.
Figure 22:
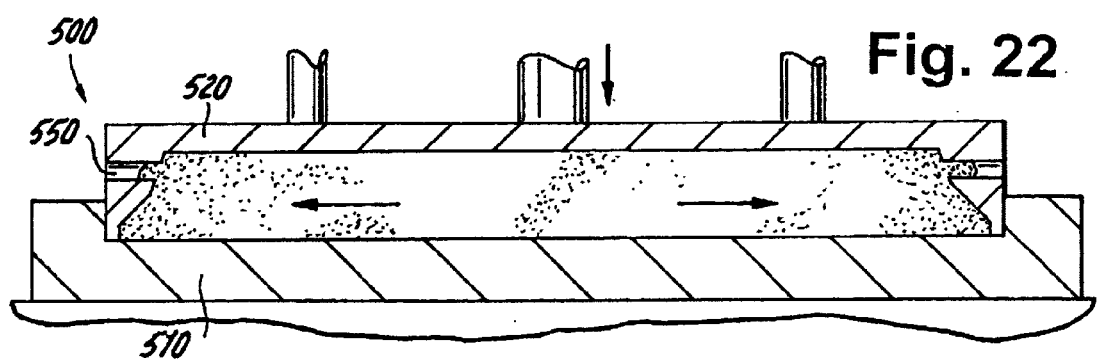
FIG. 22 is cross-sectional side elevational view of the apparatus of FIG. 21 with the mandrel being in the fully extended position.
Figure 23:
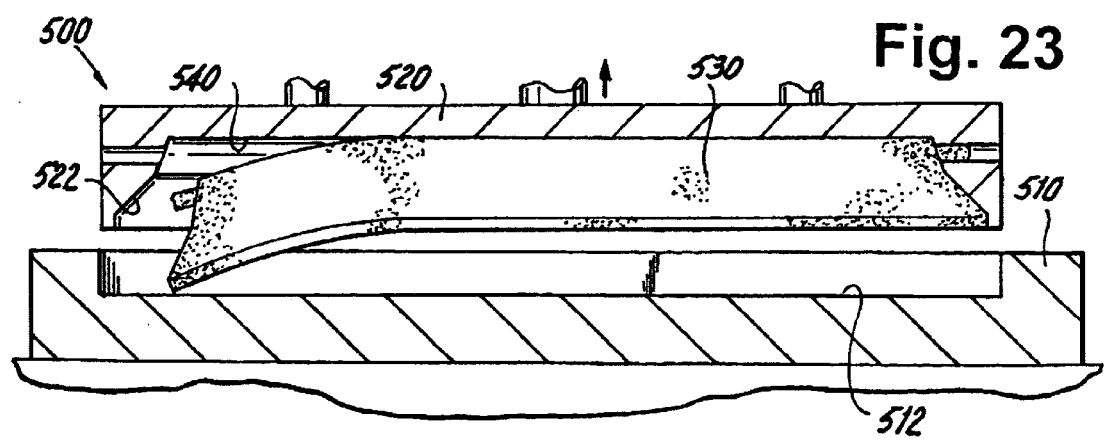
FIG. 23 is a cross-sectional side elevational view of the apparatus of FIG. 21 with the mandrel being retracted to permit removal of the article.

FIG. 20 illustrates another exemplary article 530. The article 530 is similar to the article 400 with the exception that the article 530 includes an integral ridge 534 that extends the length of the article 530. As illustrated in FIGS. 21–23, to form the article 530, the apparatus 500 is simply modified by forming a recessed feature 540 in the recessed section 522 of the mandrel plate 520. In this embodiment, the feature is a semi-circular recessed groove to form the semi-circular ridge shown in FIG. 20. The formation of the article 530 is then conducted in essentially the same manner as described above.

FIG. 22 shows another feature of the apparatus 500 in that the mandrel plate 520 includes one or more ports 550 that act as ports for releasing excess cushioning material and for releasing air, etc. from the mold cavity. Because the cushioning material preferably has a gel-like consistency, only excess cushioning material is forced through the ports 550 when compressive forces are applied to the cushioning material by the mandrel plate 520. The ports 550 also function to evacuate air and this decreases the chance that the formed cushioned article will have air bubbles, other imperfections, etc. The excess material can be directed to any number of locations, including the sides of the plate or the top of the mandrel plate 520. FIG. 23 shows the removal of the article 530.

Figure 24:
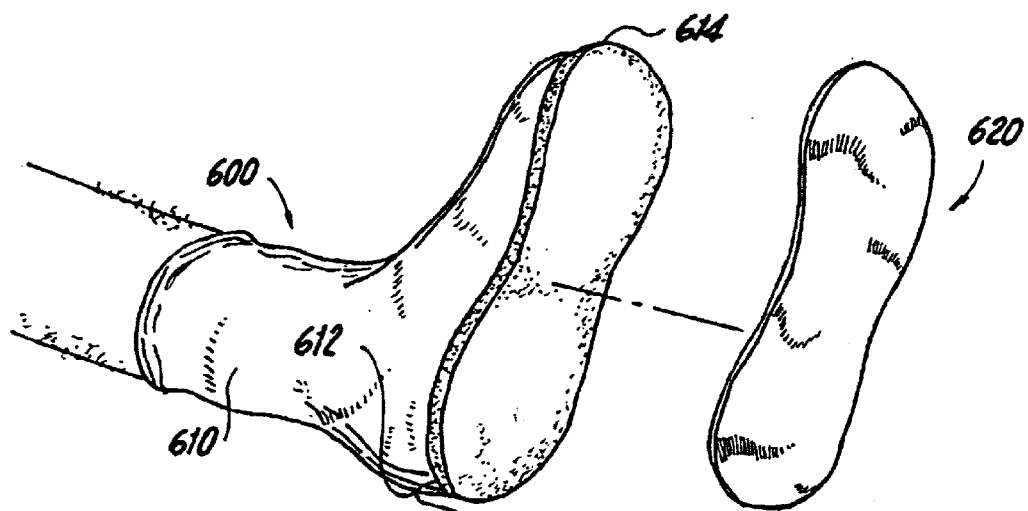
FIG. 24 is a perspective of a cushioned sock article with an optionable liner being exploded therefrom.

FIG. 24 shows another exemplary article 600 that can be formed using the compression molding process disclosed herein. In this embodiment, the article 600 is generally in the form of a pad of cushioning material. The pad 600 can assume any number of shapes and can also be provided in any number of dimensions. In one embodiment, the pad 600 is disposed on a bottommost foot portion of a sock 610 such that the pad 600 extends from the heel portion 612 to the toe portion 614. The sock 610 can be a standard athletic sock or any other type of sock (e.g., a diabetic sock). Optionally, a fabric protective sheet 620 is securely attached to the pad 600 and serves as the ground contacting surface when the sock 610 is worn.

Figure 25:
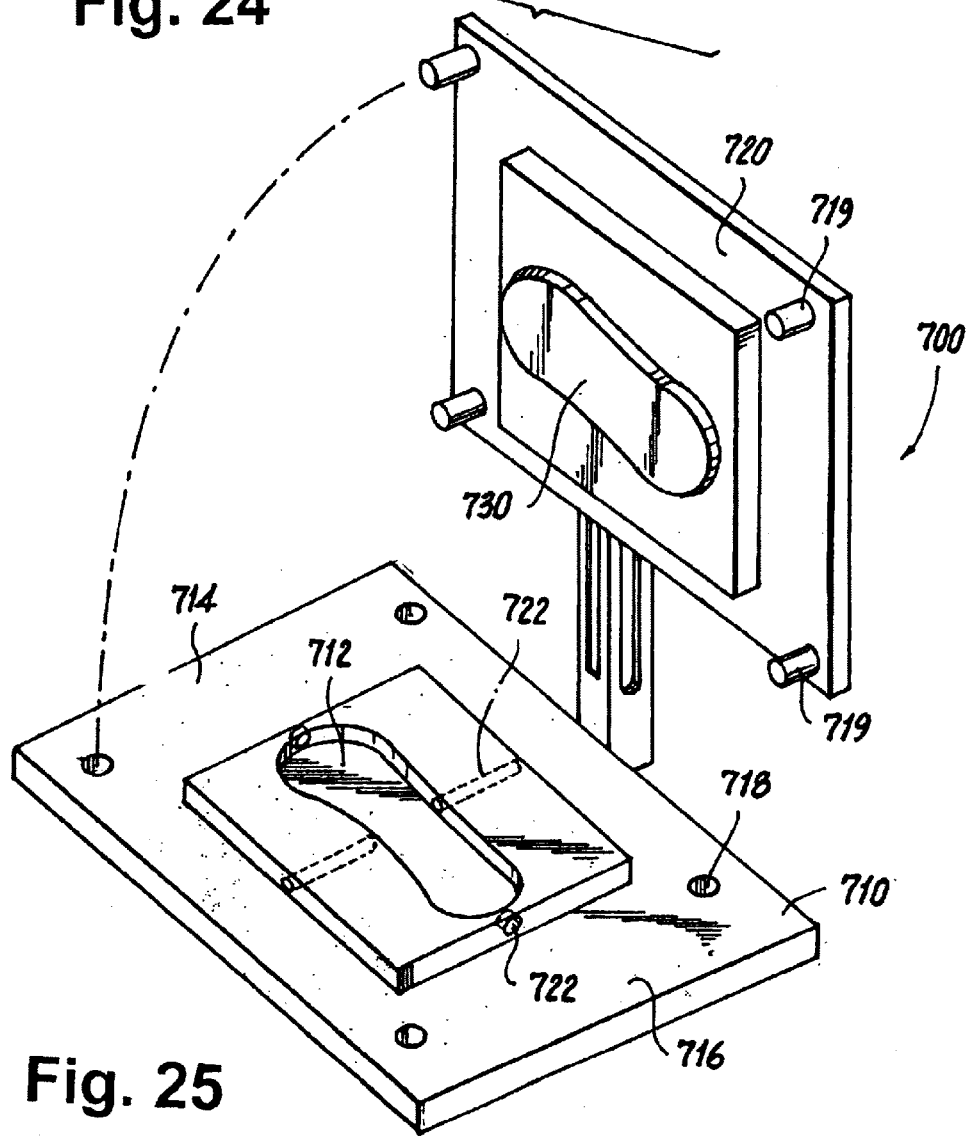
FIG. 25 is a perspective view of an exemplary apparatus for forming the sock article of FIG. 24.

The sock 610 is formed using a compression molding process that is similar to the process described hereinbefore. FIG. 25 illustrates an apparatus 700 for making the pad 600 using compression molding techniques. The apparatus 700 includes a mold body 710 having a recessed section (e.g., cavity) 712 for receiving the cushioning material and a backing article in some embodiment and a positionable mandrel plate 720 for dispersing the cushioning material under compression across the recessed section 712 so that the cushioning material spreads out across the recessed section 712 and has a predetermined thickness.

FIG. 25 shows another feature of the apparatus 700 in that the mold body 710 includes one or more ports 722 for releasing excess cushioning material. The ports 722 also function to evacuate air and this decreases the chance that the formed cushioned article will have air bubbles, other imperfections, etc. In the illustrated embodiment, the ports 722 are orientated at one end of the recessed section 712; however, it will be understood that the ports 722 can be arranged in any number of locations within the recessed section 712.

The mold body 710 preferably includes side sections 714, 716 that extend laterally from the body portion containing the recessed section 712. The side sections 714, 716 can further include apertures 718 or the like which receive complementary locating features 719 formed on the mandrel plate 720 so as to assist in locating and retaining the mandrel plate 720 against the mold body 710. The mandrel plate 720 is an elongated member that includes a block portion 730 that is configured to be received within the recessed section 712. Thus, the block portion 730 is formed on the mandrel plate 720 at a location such that when the mandrel plate 720 is closed relative to the mold body 710, the block portion 730 is received within the recessed section 712. The block portion 730 therefore has a complementary shape and complementary dimensions relative to the recessed section 712 to permit mating between the two. The mandrel plate 720 also preferably includes the locating features 719 (e.g., locating pins protruding downwardly from the mandrel plate 720) that are received in the apertures 718 when the mandrel plate 720 is mated with the mold body 710.

The apparatus 700 also includes means for mating the mandrel plate 720 with the mold body 710 under compressive forces. More specifically, any number of conventional means can be used for applying a compressive force to the mandrel plate 720 when it is properly aligned and mated with the mold body 710. The application of compressive forces to the cushioning material disposed within the recessed section 712 causes the cushioning material to be uniformly dispersed throughout the recessed section 712. In one embodiment, the means for applying compressive forces can be a pneumatic device that extends and retracts the mandrel plate 720 relative to the mold body 710, similar to the embodiment of FIGS. 7–15. In another embodiment, the means can consist of a manually driven press device where an operator engages the mandrel plate 720 and applies a force against the mandrel plate 720 to cause compression and dispersement of the cushioning material within the recessed section 712.

The recessed section 712 can be formed to have a number of different shapes and also, as illustrated, the recessed section 712 can have beveled edges 713 that define the periphery of the recessed section 712. The beveled edges 713 cause the molded product to have beveled edges.

Figure 26:
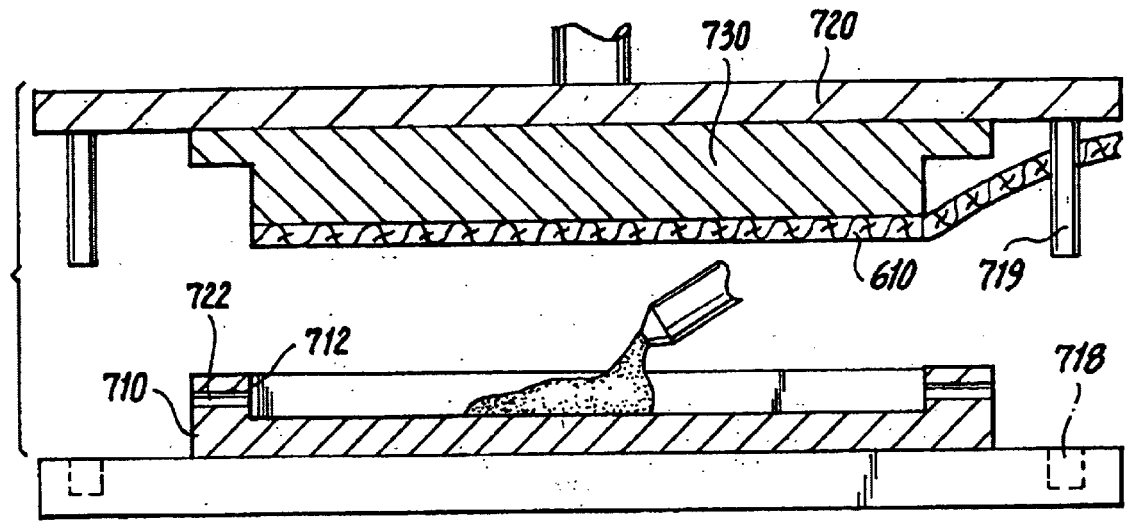
FIG. 26 is a cross-sectional side elevational view of the apparatus of FIG. 25 with a mandrel being in a retracted position with the sock arranged thereabout and the cushioning material being injected into a mold cavity.

The process of forming an article, such as pad 600, using the apparatus 700 is as follows (with reference to FIGS. 25–28). The mandrel plate 720 is initially separated from the mold body 710 and the cushion material is injected or otherwise disposed within the recessed section 712 as shown in FIG. 26. When it is desired for the pad 600 to be formed as part of an article, such as sock 610, the article can be disposed can be disposed either in the cavity 712 to formed the pad 600 on top of the article or the article can be disposed around the block portion 530 to form the pad 600 underneath the pad 600, or articles can be disposed at both locations to form the pad 600 between two articles.

Figure 27:
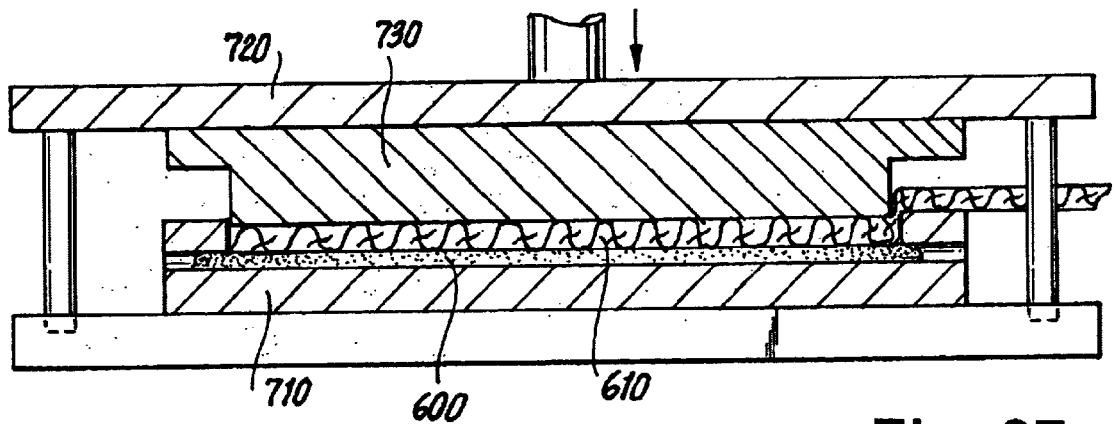
FIG. 27 is cross-sectional side elevational view of the apparatus of FIG. 26 with the mandrel in the fully extended position.

A robotic injector or the like can be used to inject a predetermined amount of cushioning material (in a liquid or molten state) into the recessed section. Preferably, the amount injected is slightly more than amount needed to form the article (in other words an overflow amount of cushioning material is injected). After the cushioning material has been injected, the mandrel plate 720 is then positioned such that the block portion 730 is aligned with and received within the recessed cavity 712. Compressive forces are applied to the mandrel plate 720 causing the block portion 730 to contact and apply a compressive force against the cushioning material that is disposed within the recessed section 712, as illustrated in FIG. 27. The block portion 730 thus effectively disperses the cushioning material across the recessed cavity 712 as the mandrel plate 720 is driven to a closed position. In the closed position, the mandrel plate 720 and the mold body 710 fully mate with one another and the distance between the block portion 730 and the surface of the recessed section 712 define the thickness of the product that is formed within the recessed section 712. Likely, as the mandrel plate 720 is driven to this closed position, some of the cushioning material (i.e., the excess amount) is driven through the ports 722 (which can be in the mold body 710 and/or the mandrel plate 720).

The cushioning material is then allowed to sufficiently cool before the mandrel plate 720 is retracted from the closed position and access is provided to the recessed section 712. Once the mandrel plate 712 is separated from the mold body 710, the article (e.g., pad 600) is removed.

The apparatus 700 includes a number of the features that are contained in the apparatus 200. More specifically, both apparatuses are configured to offer improved control over the degree of precision in forming an article of a desired thickness. Further, both apparatuses permit the contour/profile of the formed article to be readily altered depending upon the precise application and the desired characteristics that the operator wishes the article to include.

It will be appreciated that one or more characteristics of at least one of the block portion 730 and the recessed section 712 can be altered, thereby causing the formed article to have an altered profile. For example, while traditional manufacturing methods produce gel-like pads having planar surface, the present apparatus and process permit the top and/or bottom surface of the article to have an non-uniform appearance. In one embodiment, the block portion 730 does not contain a uniform shape but rather contains one or more non-uniform features, such as a protruding section or a recessed section.

Figure 28:
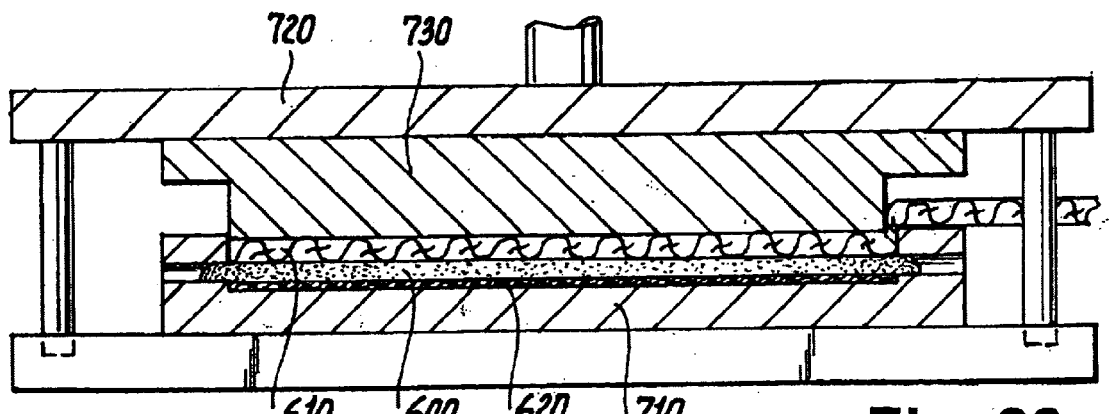
FIG. 28 is a cross-sectional side elevational view of the apparatus of FIG. 26 with the liner being disposed in the mold cavity and the mandrel being in the fully extended position.

When it is desired to form the cushion layer on a surface of an article, such as the sock 610, the above described process is slightly modified in that the sock 610 is preferably placed around the block portion 730 and the cushioning material is injected into the cavity 712 and then the mandrel plate 720 is compressed causing the cushioning material to be dispersed across the sock 610 as shown in FIG. 27. Upon cooling and disengagement of the mandrel plate 720, the cushioned pad 600 is formed on the sock 610. If it is desired that the cushioned sock article contain the fabric protective sheet 620, the fabric protective sheet 620 is disposed in the cavity 712 and the sock 610 is disposed around the block portion 730, and the mandrel plate 720 is fully extended such that the block portion 730 compresses the cushion material between the sock 610 and the sheet 620 as shown in FIG. 28. The above process is not limited to being used in combination with a sock but rather applies to any application where one or more fabric elements are formed with the pad 600. It will be appreciated that the fabric element can initially be releasably adhered to the block portion 730 so as to ensure the proper positioning of the fabric element within the recessed section 712.

Figure 29:
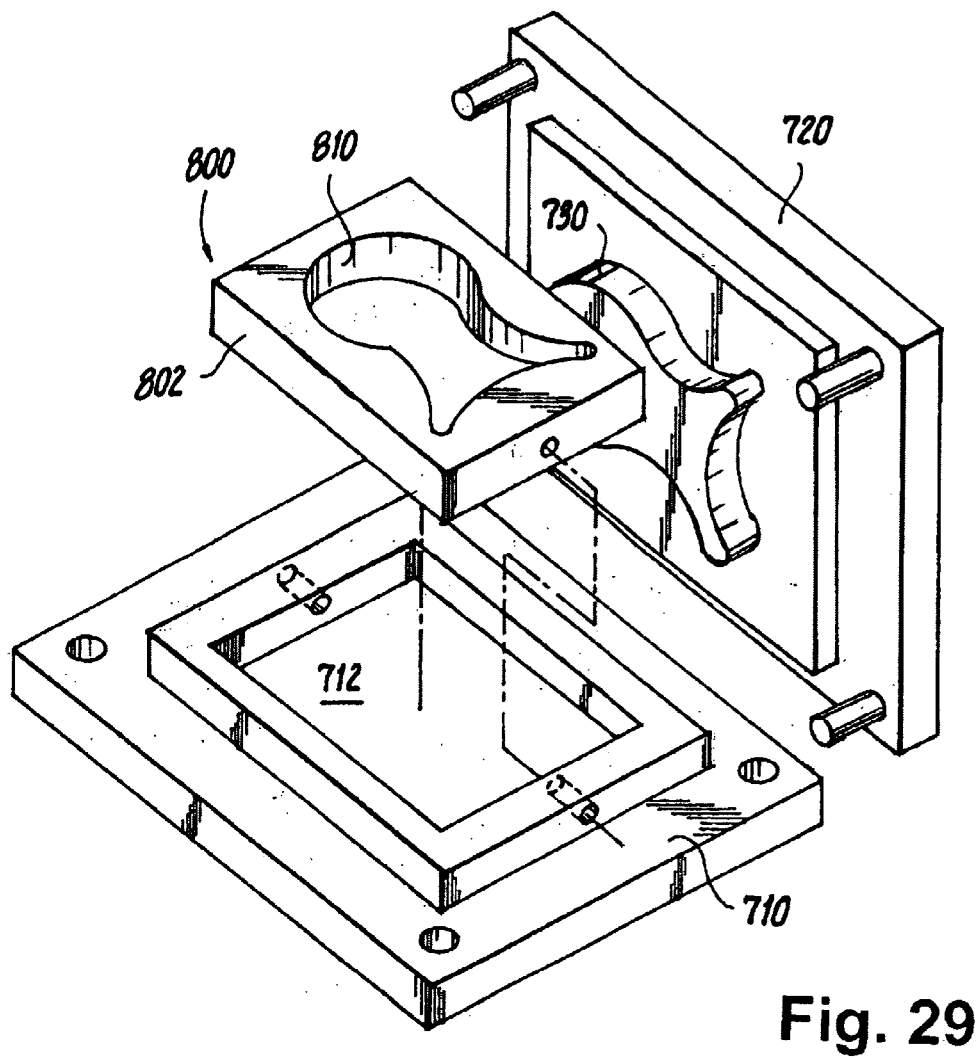
FIG. 29 is a perspective view of the apparatus of FIG. 25 with a cast member being shown.

In yet another embodiment illustrated in FIG. 29, an interchangeable cast member 800 is disposed within the recessed section 712. The cast member 800 includes a peripheral edge 802 that preferably is complementary to the peripheral edge of the recessed section 712 so that when the cast member 800 is inserted into the recessed section 712, the peripheral edge 702 is seated against the peripheral edge of the recessed section 712 such that the cast member 800 is securely retained within the recessed section 712 and does not move unnecessarily. The cast member 800 has a shaped opening 810 formed therethrough for receiving the cushioning material. It will be understood that the shaped opening 810 defines the shape of the cushioned article that is formed as a result of disposing the cushioning material within the shaped opening 810. It will further be understood that the block portion 730 must also be configured in a complementary manner such that the block portion 730 is received within the shaped opening and causes the cushioning material to be dispersed throughout the shaped opening 810.

Figure 30:
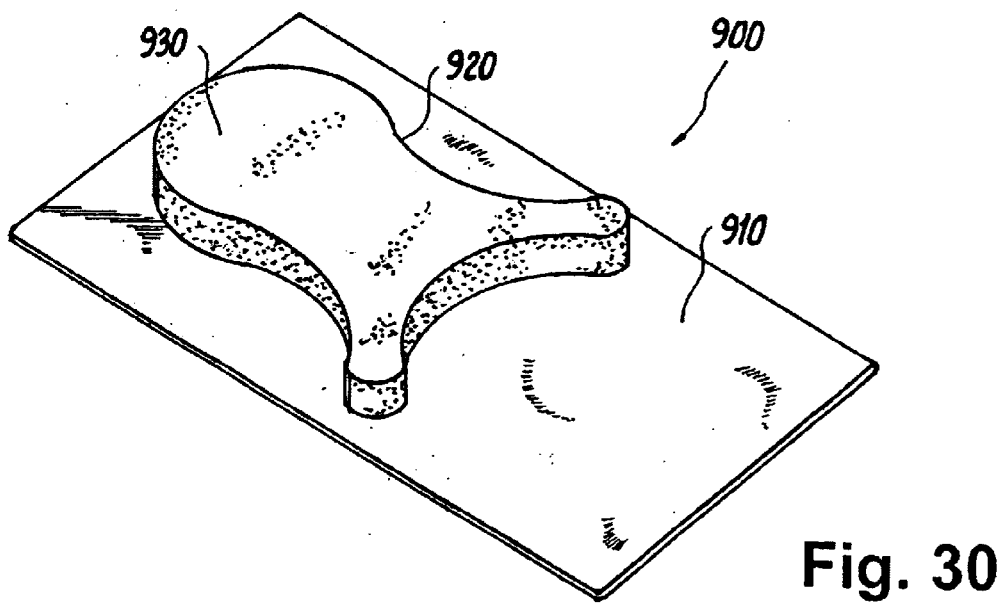
FIG. 30 is a perspective view of another article formed by the apparatus of FIG. 29.
Figure 31:
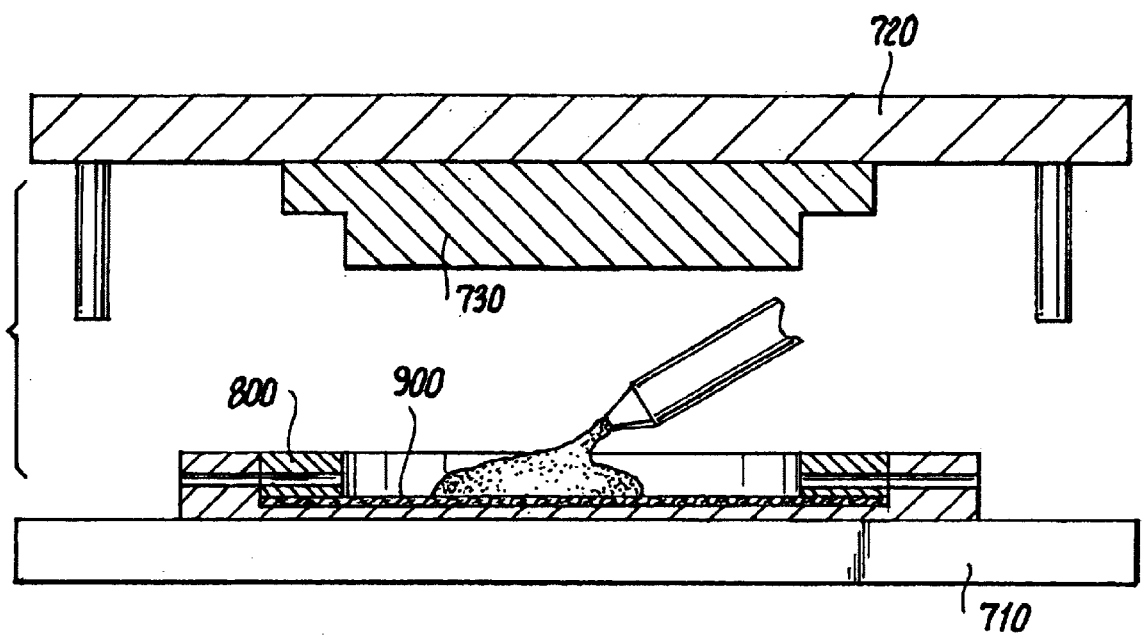
FIG. 31 is a cross-sectional side elevational view of the apparatus of FIG. 29 with the mandrel in the retracted position.
Figure 32:
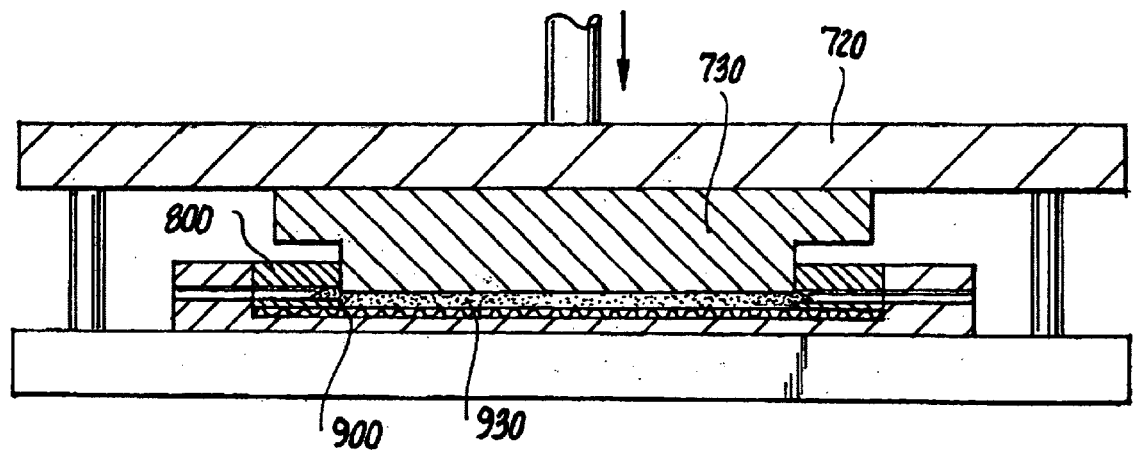
FIG. 32 is a cross-sectional side elevational view of the apparatus of FIG. 29 with the mandrel in the fully extended position.

One particular use of the cast member 800 is described with reference to FIGS. 30–32. FIG. 30 illustrates an article 900. Article 900 is preferably formed of a textile material (i.e., fabric, etc.) and includes a first portion 910 that is free of cushioning material and a second portion 920 which includes cushioning material formed in the shape of a pad 930 or the like. The article 900 is formed by first placing the article 900 in the recessed section 712 of the mold body 710. The article 900 is spread out so that it remains flush against the bottom surface of the recessed section 712. The cast member 800 is then inserted into the recessed section so that the peripheral edge 802 seats against the peripheral edge of the recessed section 712. The shaped opening 810 is thus positioned over only a section of the article 900 and the surrounding sections of the article 900 that lie underneath the cast member 800 are not exposed to the cushioning material.

The cushioning material is injected into the shaped opening 810 and the mandrel plate 720 is then closed, whereby the block portion 730 is received within the shaped opening 810 and compresses the cushioning material. Preferably, one or more ports 722 is in communication with the shaped opening 810 to permit any excess cushioning material and/or air to be discharged from the shaped opening 810. Thus, ports 722 formed in the body 710 and the cast member 800 are axially aligned. The ports 722 can also be formed in the block portion 730. Because the article 900 is disposed across the bottom of the shaped opening 810, the pad 930 is formed on top of the second portion 920 of the article 900. After cooling, the mandrel plate 720 is retracted and the cast member 800 can be removed, leaving the article 900 having the pad 930 formed thereon. As with the other embodiments, the pad 930 does not have to have a planar top or bottom surface. The block portion 730 can have a non-uniform shape, e.g., it can contain a recessed section to produce a section of increased cushion thickness or it can contain a protruding feature to reduce the thickness in a localized area of the article. The peripheral edge of the article can be shaped by contouring the shape of the peripheral edge of the cast member 800 that defines the shaped opening 810.

As with the other embodiment, the recessed section 712 and the cast member 800 can be used to produce a cushion pad that is not a part of or coupled to another article (e.g., a fabric). The cushion pad can be distributed for later attachment to an article or the cushion pad can be used by itself (i.e., around a toe or finger).

As is the case with all of the embodiments, the apparatus 700, with or without the use of the cast member 800, permits the thickness of the cushion pad to be controlled with improved precision since the distance between the block portion 730 and the recessed section 712 can be readily determined and controlled. Further by interchanging the components, the profiles of the block portion 730 and/or the recessed section 712 can be varied, thereby changing the profile of the formed cushion article.

It will be appreciated that the disclosed compression molding apparatuses can be used to produce a number of different types of articles and those articles disclosed herein are merely exemplary in nature and not limiting of the scope of the present disclosure. The present application thus discloses cushioned sleeve members that advantageously are constructed so that the interface between the residual limb and the prosthetic device is improved by eliminating the distal seam that extends across the sensitive distal end of the residual limb. Further, the present application provides methods that permit the thickness of the cushion layer to be controlled with enhanced precision and also permits the profile (contour) of the cushion layer to be readily changed.

While the invention has been particularly shown and described with reference to preferred embodiments thereof, it will be understood by those skilled in the art that various changes in form and details may be made therein without departing from the spirit and scope of the invention.

What is claimed is:

1. A process for forming a final molded article in the form of a cushion layer of a preselected thickness on an inside of a prosthetic liner body, the process comprising the steps of:

providing an apparatus including a mold having a cavity formed therein and a mandrel that is positionable between a retracted position and an extended position, wherein in the extended position, at least a portion of the mandrel is received within the cavity, wherein the distance between a first point alone an inner surface of the mold cavity and a second point along an outer surface of the mandrel when it is disposed therein represents a thickness of the final molded article, wherein the distance is measured along an axis that extends only across an empty space formed between the inner and outer surfaces;

disposing the prosthetic liner body into the mold cavity;

disposing a quantity of cushioning material, in its liquid state, into the inside of the prosthetic liner such that the cushioning material pools at a distal end of the prosthetic liner, the quantity being a sufficient quantity to form the cushion layer of the preselected thickness, wherein the cushioning material comprises a thermoplastic elastomer that forms the final molded article and is selected so that the cooled resulting final molded article can be freely rolled off the mandrel;

directing the mandrel into the inside of the prosthetic liner until the mandrel is positioned in the extended position, the driving action of the mandrel causing the cushioning material to be dispersed between the mandrel and the prosthetic liner, thereby forming the cushioning layer of the preselected thickness;

cooling the cushioning material to form a cushioned prosthetic liner; and withdrawing the mandrel from the mold cavity such that the final molded article can be removed therefrom.

2. The process of claim 1, wherein at least a distal end of the mold cavity is in communication with a vacuum source such that a vacuum is selectively applied to the mold cavity to assist in positioning of the prosthetic liner body.

3. The process of claim 1, wherein the positionable mandrel is part of a programmable pneumatic device which drives the mandrel between the retracted position and the extended position.

4. The process of claim 3, wherein the mandrel is an elongated structure supported at one end with a base, the base being connected to two or more pistons of pneumatic cylinders for pneumatically driving the mandrel between the retracted position and the extended position.

5. The process of claim 1, wherein in the retracted position, the mandrel is spaced a predetermined distance from the prosthetic liner body, the predetermined distance corresponding to the preselected thickness of the cushioned prosthetic liner.

6. The process of claim 1, wherein the mandrel comprises an elongated structure having a first supported end and an opposing rounded distal end.

7. The process of claim 6, wherein the mandrel tapers inwardly along a length thereof from the first end to the rounded distal end.

8. The process of claim 1, further including the step of:

contouring the cushion layer by altering a surface of the mandrel.

9. The process of claim 1, wherein the mandrel has a non-uniform shape.

10. The process of claim 1, further including the step of:
forming a recessed section along the length of the mandrel, the recessed section causing the formation of a section of increased thickness along the length of the cushion layer of the cushioned prosthetic liner.

11. The process of claim 1, further including the step of:
forming a protruding section along the length of the mandrel, the protruding section causing the formation of a section of decreased thickness along the length of the cushion layer of the cushioned prosthetic liner.

12. The process of claim 1, wherein the mandrel has an uneven taper along its length in that a section of the distal end has an increased taper relative to surrounding sections of the distal end.

13. A process for forming a cushion layer of a preselected thickness on an inside of prosthetic liner body, the process comprising the steps of:
providing an apparatus including a mold having a cavity formed therein and a mandrel that is positionable between a retracted position and an extended position, wherein in the extended position, at least a portion of the mandrel is received within the cavity;
disposing the prosthetic liner body into the mold cavity;
disposing a quantity of cushioning material into the inside of the prosthetic liner such that the cushioning material pools at a distal end of the prosthetic liner, the quantity being a sufficient quantity to form the cushion layer of the preselected thickness;
directing the mandrel into the inside of the prosthetic liner until the mandrel is positioned in the extended position, the driving action of the mandrel causing the cushioning material to be dispersed between the mandrel and the prosthetic liner, thereby forming the cushioning layer of the preselected thickness; cooling the cushioning material to form a cushioned prosthetic liner; and
withdrawing the mandrel from the mold cavity such that the cushioned prosthetic liner can be removed therefrom, wherein the mandrel includes a spring-based element at or proximate to the first end, the spring-biased element being a ring-shaped element surrounding the mandrel and being biased against the prosthetic liner body so as to enclose the space between the mandrel and the prosthetic liner body, thereby preventing cushioning material from being discharged from the cavity.

14. The process of claim 1, wherein the cushioning material is a gel composition.

15. The process of claim 14, wherein the gel composition comprises a block copolymer and mineral oil.

16. The process of claim 15, wherein the block copolymer is a polystyrene-poly(ethylene-ethylene/propylene)-polystyrene (SEEPS) block copolymer.

17. The process of claim 1, wherein the mandrel has a substantially conical cross-sectional shape.

18. A process for forming an article formed of a layer of cushioning material that has a preselected thickness, the process comprising the steps of:
providing an apparatus including a mold having a cavity formed therein and a mandrel that is positionable between a retracted position and an extended position, wherein in the extended position, at least a portion of the mandrel is received within the cavity;
disposing a prosthetic liner body having at least two fabric pieces, one of the fabric pieces being a distal end piece that is attached to at least one other fabric piece along a circumferential edge of the distal end piece, the distal end piece being free of a transverse seam extending across the distal end piece, into the mold cavity, the distal end piece being disposed at one end of the at least one other fabric piece and having a substantially annular shape prior to and after attachment to the at least one other fabric piece;
disposing a quantity of cushioning material into an inside of the prosthetic liner such that the cushioning material pools at a distal end of the prosthetic liner, the quantity being a sufficient quantity to form the cushioning layer of the preselected thickness;
directing the mandrel into the inside of the prosthetic liner until the mandrel is positioned in the extended position, the driving action of the mandrel causing the cushioning material to be dispersed between the mandrel and the prosthetic liner, thereby forming the cushioning layer of preselected thickness;
cooling the cushioning material to form the cushioning layer; and
withdrawing the mandrel from the mold cavity such that the article can be removed therefrom.

19. The process of claim 18, wherein the positionable mandrel is part of a programmable pneumatic device which drives the mandrel between the retracted position and the extended position.

20. The process of claim 19, wherein the mandrel is an elongated structure supported at one end with a base, the base being connected to two or more pistons of pneumatic cylinders for pneumatically driving the mandrel between the retracted position and the extended position.

21. The process of claim 18, wherein in the retracted position, the mandrel is spaced a predetermined distance from an inner wall of the prosthetic liner, the predetermined distance corresponding to the preselected thickness of the cushioning layer.

22. The process of claim 18, wherein the mandrel comprises an elongated structure having a first supported end and an opposing rounded distal end.

23. The process of claim 22, wherein the mandrel tapers inwardly along a length thereof from the first end to the rounded distal end.

24. The process of claim 18, further including the step of:
contouring the article by altering a surface of the mandrel.

25. The process of claim 18, wherein the mandrel has a non-uniform shape.

26. The process of claim 18, further including the step of:
forming a recessed section along the length of the mandrel, the recessed section causing the formation of a section of increased thickness along the length of the article.

27. The process of claim 18, further including the step of:
forming a protruding section along the length of the mandrel, the protruding section causing the formation of a section of decreased thickness along the length of the article.

28. The process of claim 18, wherein the mandrel has an uneven taper along its length in that a section of the distal end has an increased taper relative to surrounding sections of the distal end.

29. The process of claim 18, wherein the cushioning material is a gel composition.

30. The process of claim 29, wherein the gel composition comprises a block copolymer and mineral oil.

31. The process of claim 30, wherein the block copolymer is a polystyrene-poly(ethylene-ethylene/propylene)-polystyrene (SEEPS) block copolymer.

32. The process of claim 18, wherein in the extended position, there is a gap between a distal end of the mandrel and a-closed distal end of the prosthetic liner, the cushioning material settling within this gap and flowing around an outer surface of the mandrel so as to form a tube-like article having a closed distal end.

33. A process for forming an article formed of a cushioning material and having a preselected thickness, the process comprising the steps of:
provided an apparatus including a mold having a cavity formed therein and a mandrel plate that at least includes a mandrel block that is adapted to be received within the mold cavity;
disposing a fabric layer to a bottom surface of the cavity;
inserting a cast member into the cavity, the cast member having a through opening formed therein for receiving the cushioning material, wherein the shape of the article is controlled by a shape of the through opening, the cast member being disposed on top of the fabric layer such that the fabric layer is exposed in an area of the through opening the mandrel block having a shape complementary to the through opening to permit the mandrel block to be received in the through opening;
determining the preselected thickness of the article and disposing a sufficient quantity of cushioning material into the cast member to form the article to the preselected thickness, the cushioning material pooling within the cast member;
directing the mandrel block into the inside of the cast member so that the mandrel block contacts the cushioning material and spreads the cushioning material throughout the cast member, the mandrel block being driven to an extended position where the distance between a bottom surface of the mandrel block and the fabric is approximately equal to the preselected thickness;
cooling the cushioning material to form the cushioning layer; and
withdrawing the mandrel block from the cast member such that the article can be removed therefrom.

34. The process of claim 33, wherein the mandrel block has an outer dimensions that is about equal to an inner dimension of the cast member so that a peripheral edge of the mandrel block is in intimate contact with a peripheral edge of a wall that defines the through opening, thereby preventing cushioning material from flowing between the mandrel block and the wall that defines the through opening.

35. The process of claim 33, wherein the mandrel block and the cast member have complementary shapes selected from the group consisting of: circles, ovals, squares, rectangles, diamonds, and triangles.

36. The process of claim 33, wherein the step of driving the mandrel comprises the steps of:
manually closing the mandrel plate such that the mandrel block is received within the through opening; and
applying a compressive force against the mandrel block which is transferred to the cushioning material to cause the cushioning material to spread across the cast member.

37. The process of claim 33, wherein the step of driving the mandrel comprises the step of:
pneumatically closing the mandrel plate such that the mandrel block is received within the through opening, the mandrel block being driven to the extended position, whereby a compressive force is applied to the cushioning material to cause the cushioning material to spread across the cast member.

38. The process of claim 33, further including the step of:
disposing a first fabric layer to a bottom surface of the cavity prior to disposing the cushioning material into the cavity, and
disposing a second fabric layer around the mandrel block prior to driving the mandrel block to the extended position, the cushioning layer being formed between the first and second fabric layers.

39. The process of claim 33, further including the step of:
forming a discharge port in the mold such that the discharge port is in communication with the cast member and permits at least one of excess cushioning material and air to be evacuated from the cast member.

40. The process of claim 33, further including the step of:
forming a discharge port in the mandrel block such that the discharge port is in communication with the cavity and permits at least one of excess cushioning material and air to be evacuated from the cavity.

* * * * *

UNITED STATES PATENT AND TRADEMARK OFFICE
CERTIFICATE OF CORRECTION

PATENT NO. : 6,852,269 B2
DATED : February 8, 2005
INVENTOR(S) : John D. Eberle et al.

It is certified that error appears in the above-identified patent and that said Letters Patent is hereby corrected as shown below:

Column 22,
Line 20, after "cavity", -- ,the liner body being formed of at least two separate fabric pieces, one of the fabric pieces being a distal end piece that is attached to at least one other fabric piece along a circumferential edge of the distal end piece, the distal end piece defining a closed end of the liner body and being free of a transverse seam extending acrosss the distal end piece -- has been inserted.

Column 24,
Line 6, after "piece", -- to define a closed end of the liner body -- has been inserted;
Lines 6-7, "annular" has been replaced with -- circular --;

Signed and Sealed this

Tenth Day of May, 2005

JON W. DUDAS
*Director of the United States Patent and Trademark Office*